(12) United States Patent
Rodriguez et al.

(10) Patent No.: US 8,617,467 B2
(45) Date of Patent: Dec. 31, 2013

(54) HIGH-PRESSURE STERILIZATION TO TERMINALLY STERILIZE PHARMACEUTICAL PREPARATIONS AND MEDICAL PRODUCTS

(75) Inventors: Alfredo Rodriguez, Arlington Heights, IL (US); Barrett E. Rabinow, Skokie, IL (US); Mark Doty, Grayslake, IL (US); Jamie Konkel, Island Lake, IL (US)

(73) Assignees: Baxter International Inc., Deerfield (IL); Baxter Healthcare SA, Glattpark (Opifkon) (CH)

( * ) Notice: Subject to any disclaimer, the term of this patent is extended or adjusted under 35 U.S.C. 154(b) by 1393 days.

(21) Appl. No.: 10/946,885

(22) Filed: Sep. 22, 2004

(65) Prior Publication Data

US 2005/0135963 A1 Jun. 23, 2005

Related U.S. Application Data

(60) Provisional application No. 60/505,235, filed on Sep. 22, 2003.

(51) Int. Cl.
*A61L 2/00* (2006.01)

(52) U.S. Cl.
USPC .............................................. 422/39; 422/25

(58) Field of Classification Search
USPC ...................................................... 422/25, 39
See application file for complete search history.

(56) References Cited

U.S. PATENT DOCUMENTS

| | | | |
|---|---|---|---|
| 3,113,986 A | 12/1963 | Breslow et al. | |
| 4,210,686 A | 7/1980 | Gajewski et al. | |
| 4,226,952 A | 10/1980 | Halasa et al. | |
| 4,417,753 A | 11/1983 | Bacehowski et al. | |
| 4,608,278 A | 8/1986 | Frank et al. | |
| 4,764,604 A | 8/1988 | Muller | |
| 4,916,198 A | 4/1990 | Scheve et al. | |
| 5,047,485 A | 9/1991 | DeNicola, Jr. | |
| 5,091,188 A | 2/1992 | Haynes | |
| 5,100,591 A | 3/1992 | Leclef et al. | |
| 5,118,528 A | 6/1992 | Fessi et al. | |
| 5,145,684 A | 9/1992 | Liversidge et al. | |
| 5,298,262 A | 3/1994 | Na et al. | |
| 5,336,507 A | 8/1994 | Na et al. | |
| 5,346,702 A | 9/1994 | Na et al. | |
| 5,416,169 A | 5/1995 | Saito et al. | |
| 5,470,583 A | 11/1995 | Na et al. | |
| 5,531,925 A | 7/1996 | Landh et al. | |
| 5,560,932 A | 10/1996 | Bagchi et al. | |
| 5,577,369 A | 11/1996 | Becker et al. | |
| 5,605,936 A | 2/1997 | DeNicola, Jr. et al. | |
| 5,662,883 A | 9/1997 | Bagchi et al. | |
| 5,665,331 A | 9/1997 | Bagchi et al. | |
| 5,716,642 A | 2/1998 | Bagchi et al. | |
| 5,780,062 A | 7/1998 | Frank et al. | |
| 5,849,843 A | 12/1998 | Laurin et al. | |
| 5,935,847 A | 8/1999 | Smith et al. | |
| 5,998,019 A | 12/1999 | Rosenbaum et al. | |
| 6,004,636 A | 12/1999 | Nicola et al. | |
| 6,017,572 A | 1/2000 | Meyer | |
| 6,017,598 A | 1/2000 | Kreischer et al. | |
| 6,024,994 A * | 2/2000 | Jacobson et al. | 426/74 |
| 6,086,936 A * | 7/2000 | Wilson et al. | 426/521 |
| 6,120,732 A * | 9/2000 | Toledo et al. | 422/39 |
| 6,132,395 A | 10/2000 | Landau et al. | |
| 6,143,211 A | 11/2000 | Mathiowitz et al. | |
| 6,162,392 A * | 12/2000 | Platz et al. | 422/26 |
| 6,177,115 B1 | 1/2001 | Meyer | |
| 6,207,215 B1 | 3/2001 | Wilson et al. | |
| 6,235,224 B1 | 5/2001 | Mathiowitz et al. | |
| 6,242,020 B1 * | 6/2001 | Jacobson et al. | 426/74 |
| 6,267,989 B1 * | 7/2001 | Liversidge et al. | 424/489 |
| 6,270,723 B1 | 8/2001 | Laugharn, Jr. et al. | |
| 6,271,351 B1 | 8/2001 | Gawryl et al. | |
| 6,309,723 B1 | 10/2001 | Ding et al. | |
| 6,491,882 B1 | 12/2002 | Van Den Berg et al. | |
| 6,635,223 B2 | 10/2003 | Maerz | |
| 6,673,311 B1 * | 1/2004 | Sotoyama et al. | 422/1 |
| 6,696,019 B2 | 2/2004 | Laugharn, Jr. et al. | |
| 6,869,617 B2 | 3/2005 | Kipp et al. | |
| 6,884,436 B2 | 4/2005 | Kipp et al. | |
| 2001/0042932 A1 | 11/2001 | Mathiowitz et al. | |
| 2001/0051197 A1 * | 12/2001 | Yang et al. | 426/74 |

(Continued)

FOREIGN PATENT DOCUMENTS

| | | |
|---|---|---|
| DE | 19905159 | 8/2000 |
| EP | 01112008 | 7/2001 |
| EP | 01112091 | 7/2001 |
| EP | 01201252 | 5/2002 |
| FR | 2750011 | 12/1997 |
| FR | 2838969 | 10/2003 |
| JP | 63-169947 | 7/1988 |
| JP | 03-068365 | 3/1991 |
| JP | 2002-537024 | 11/2002 |
| JP | 2003-250866 | 9/2003 |

(Continued)

OTHER PUBLICATIONS

International Search Report re application No. PCT/US2004/031107, dated Sep. 22, 2004.
Meyer et al., "High-Pressure Sterilization of Foods," *Food Technology*, 54(11):67-72 (Nov. 2000).
Na et al., "Cloud Point of Nonionic Surfactants: Modulation with Pharmaceutical Excipients,"*Pharm. Res.*, 16(4):562-568 (1999).
Berlin University of Technology assessing the experimental designs of Hayakawa et al. and Sojka et al. (8 pp.).
Comparing single and double pulses of high pressure and heat to sterilize foods (7 pp.).

(Continued)

*Primary Examiner* — Regina M Yoo
(74) *Attorney, Agent, or Firm* — Marshall, Gerstein & Borun LLP

(57) ABSTRACT

The present invention provides a process for sterilizing a system, preferably a pharmaceutical preparation such as a dispersion of small particles or droplets of a pharmaceutically active compound using high pressure terminal sterilization techniques and products therefrom.

21 Claims, 8 Drawing Sheets

(56) References Cited

U.S. PATENT DOCUMENTS

| | | | |
|---|---|---|---|
| 2002/0076347 | A1 | 6/2002 | Maerz |
| 2002/0168402 | A1 | 11/2002 | Kipp et al. |
| 2002/0176935 | A1* | 11/2002 | Kipp et al. ............... 427/213.3 |
| 2002/0182107 | A1 | 12/2002 | Laugharn et al. |
| 2003/0059472 | A1 | 3/2003 | Brynjelsen et al. |
| 2003/0103863 | A1 | 6/2003 | Grislain et al. |
| 2003/0141301 | A1 | 7/2003 | D'Evelyn et al. |
| 2003/0211083 | A1 | 11/2003 | Vogel et al. |
| 2003/0228239 | A1* | 12/2003 | Meyer et al. ................ 422/39 |
| 2004/0071842 | A1 | 4/2004 | Van Schepdael et al. |
| 2004/0151620 | A1 | 8/2004 | Laugharn, Jr. et al. |
| 2004/0229771 | A1 | 11/2004 | Deppisch et al. |
| 2005/0037083 | A1 | 2/2005 | Brynjelsen et al. |
| 2005/0152820 | A1 | 7/2005 | D'Evelyn et al. |

FOREIGN PATENT DOCUMENTS

| | | | | |
|---|---|---|---|---|
| WO | WO-95/08275 | 3/1995 | | |
| WO | WO 97/14407 | 4/1997 | | |
| WO | WO-97/21361 | 6/1997 | | |
| WO | WO-97/49305 | 12/1997 | | |
| WO | WO 9857967 A1 * | 12/1998 | ............... | C07D 3/14 |
| WO | WO 9921442 A1 * | 5/1999 | ............... | A23L 3/16 |
| WO | WO-99/29187 | 6/1999 | | |
| WO | WO-99/61146 | 12/1999 | | |
| WO | WO-00/48641 | 8/2000 | | |
| WO | WO-01/54737 | 8/2001 | | |
| WO | WO-02/45528 | 6/2002 | | |
| WO | WO-02/056824 | 7/2002 | | |
| WO | WO-2004/002540 | 1/2004 | | |
| WO | WO 2004/056666 | 7/2004 | | |
| WO | WO-2004/091309 | 10/2004 | | |
| WO | WO-2005/030273 | 4/2005 | | |
| WO | WO-2005/041694 | 5/2005 | | |
| WO | WO-2006/110051 | 10/2006 | | |

OTHER PUBLICATIONS

Kinetics of microbial inactivation for alternative food processing technologies. High pressure processing, U.S. Food and Drug Administration, Center for Food Safety and Applied Nutrition, Jun. 2, 2000. Downloaded from the Internet on Apr. 13, 2005: <http://www.unusualresearch.com/GovLab/FDA/ift/ift-hpp.html> (43 pp.).
Microbiology, packaging, HACCP & ingredients, Book II, In: Downing, *A Complete Course in Canning and Related Processes*, pp. iii, Preface, 40-49, 62-102 (1996).
Reproduction of Methods of D2 (Hayakawa et al.) (5 pp.).
Sterlization, Webster's Third New International Dictionary, p. 2238.
Aleman et al., "Pulsed ultra high pressure treatments for pasteurization of pineapple juice", *J. Food Sci*, 61:388-90 (1996).
Carpenter et al., "High-pressure disaggregation and folding of recombinant proteins; Examples and production cost comparison", *BioProcess Int.*, 46-54 (May 2005).
Chen et al., "Modeling the combined effect of high hydrostatic pressure and mild heat on the inactivation kinetics of Listeria monocytogenes Scott A in whole milk", *Innovative Food Science and Emerging Technologies*, 4:25-34 (2003).
Claeys et al., "Review: are intrinsic TTIs for thermally processed milk applicable for high-pressure processing assessment?", *Innovative Food Science and Technologies*, 4:1-14 (2003).
Clouston et al., "Initiation of germination and inactivation of *Bacillus pumilus* spores by hydrostatic pressure", *J. Bacteriology*, 97:684-90 (1969).
Clouston et al., "Kinetics of initiation of germination of *Bacillus pumilus* spores by hydrostatic pressure", *J. Bacteriology*, 103:140-3 (1970).
Cooker et al., "Effect of icodextrin peritoneal dialysis solution on cell proliferation in vitro", downloaded from the Internet on May 19, 2005 at: <http://www.advancesinpd.com/adv99/99-1-4effect.html>.
De Heij et al., "Sterilisation—only better", *New Food*, pp. 56-61 (2005).

Disteche et al., "The effect of pressure on the dissociation of carbonic acid from measurements with buffered glass electrode cells", *J. Electrochem. Soc: Electrochemical Science*, 114:330-40 (1967).
Drake et al., "High pressure treatment of milk and effects on microbiological and sensory quality of cheddar cheese", *J. Food Sci.*, 62:843-5, 860 (1997).
El'Yanov et al., "Some quantitative relationships for ionization reactions at high pressures", *Aust. J. Chem.*, 28:945-54 (1975).
El'Yanov, "Linear free energy relationship and some quantitative regularities of the effect of pressure on chemical reactions", *Aust. J. Chem.*, 28:933-43 (1975).
Erixon et al., "PD fluids contain high concentrations of cytotoxic GDPs directly after sterlization", *Perit. Dial. Int.*, 24:392-8 (2004).
Eyring et al., "The activated complex in chemical reactions", *J. Chem. Phys.*, 3:107-15 (1935).
Fornari et al., "Inactivation of *Bacillus endospores* by high-pressure treatment", *Industria Conserve*, 70:259-65 (1995).
Hawley et al., "Reversible pressure-temperature denaturation of chymotrypsinogen", *Biochem.*, 10:2436-42 (1971).
Hayakawa et al., "Application of high pressure spore inactivation and protein denaturation", *J. Food Sci.*, 59:159-63 (1994).
Hayakawa et al., "Mechanism of high pressure denaturation of proteins", *Lebensm.-Wiss.u.-Technol.*, 29:756-62 (1996).
Hayakawa et al., "Oscillatory compared with continuous high pressure sterilization on *Bacillus stearothermophilus* spores", *J Food Sci.*, 59:164-7 (1994).
Heremans, "High pressure effects on proteins and other biomolecules", *Ann. Rev. Biophys. Bioeng.*, 11:1-21 (1982).
Kim et al., "Low glucose degradation products dialysis solution modulates the levels of surrogate markers of peritoneal inflammation, integrity, and angiogenesis: preliminary report", *Nephrology*, 8:S28-S32 (2003).
Kitamura et al., "Reaction volume of protonic ionization for buffering agents. Prediction of pressure dependence of pH and pOH", *J. Sol. Chem.*, 16:715-25 (1987).
Kjellstrand et al., "Temperature: the single most important factor for degradation of glucose fluids during storage", *Perit. Dial. Int.*, 24:385-91 (2004).
Maggi et al., "Effects of combined high pressure-temperature treatments on *Clostridium sporogenes* spores in liquid media", *Industria Conserve*, 71:8-14 (1996).
Mallidis et al., "Effect of simultaneous application of heat and pressure on the survival of bacterial spores", *J. Applied Bacteriology*, 71:285-8 (1991).
Pressl et al., "High pressure cell for small- and wide-angle x-ray scattering", *Rev. Sci. Instrum.*, 68:4588-92 (1997).
Rodriguez et al., "Model of the inactivation of bacterial spores by moist heat and high pressure", *J. Food Sci.*, 69:E367-E373 (2004).
Rovere et al., "High pressure heat treatments: Evaluation of the sterilizing effect and of thermal damage", *Industria Conserve*, 71:473-83 (1996).
Rovere et al., "Modelling and calculation of the sterilising effect in high pressure heat-treatments", *Industria Conserve*, 73:303-15 (1998).
Sale et al., "Inactivation of bacterial spores by hydrostatic pressure", *J. Gen. Microbiol.*, 60:323-34 (1970).
Sojka et al., "Effects of rapid pressure changes on the inactivation of *Bacillus subtilis* spores", *Pharm. Ind.*, 59:436-8 (1997).
Sturgeon et al., "Degradation of dextrose during heating under similated sterilization", *J. Parenteral Drug Assoc.*, pp. 175-82 (1980).
Tauscher, "Pasteurization of food by hydrostatic high pressure: chemical aspects", *Z. Lebensm Unters Forsch*, 200:3-13 (1995).
Wieczorowska-Tobis et al., "Evidence for less irritation to the peritoneal membrane in rats dialyzed with solutions low in glucose degradation products", *Perit. Dial. Int.*, 24:48-57 (2004).
Wynne-Jones et al., "The absolute rate of reactions in condensed phases", *J. Chem. Phys.*, 3: 492-502 (1935).
Japanese office action from corresponding Japanese Patent Application No. 2006-527152, dated Oct. 18, 2010.

* cited by examiner

NORMAL MICELLE (L1)

REVERSE MICELLE (L2)

LAMELLAR

NORMAL HEXAGONAL (H1)

CUBIC

INITIAL PARTICLE SIZE DISTRIBUTION OF THE 1% ITRACONAZOLE NANOSUSPENSION.

PARTICLE SIZE DISTRIBUTION OF THE 1% ITRACONAZOLE NANOSUSPENSION AFTER NORMAL AUTOCLAVING FOR 15 MINUTES AT 121° C.

FIG.9

HIGH-PRESSURE STERILIZATION CYCLE USED TO PROCESS A 1% ITRACONAZOLE NANOSUSPENSION CONTAINING 0.1% POLOXAMER 188, 0.1% DEOXYCHOLATE, AND 2.2% GLYCERIN. THE RED LINE IS THE TEMPERATURE IN CELSIUS, THE BLUE LINE IS THE PRESSURE IN MPa, AND THE TIME IS IN SECONDS.

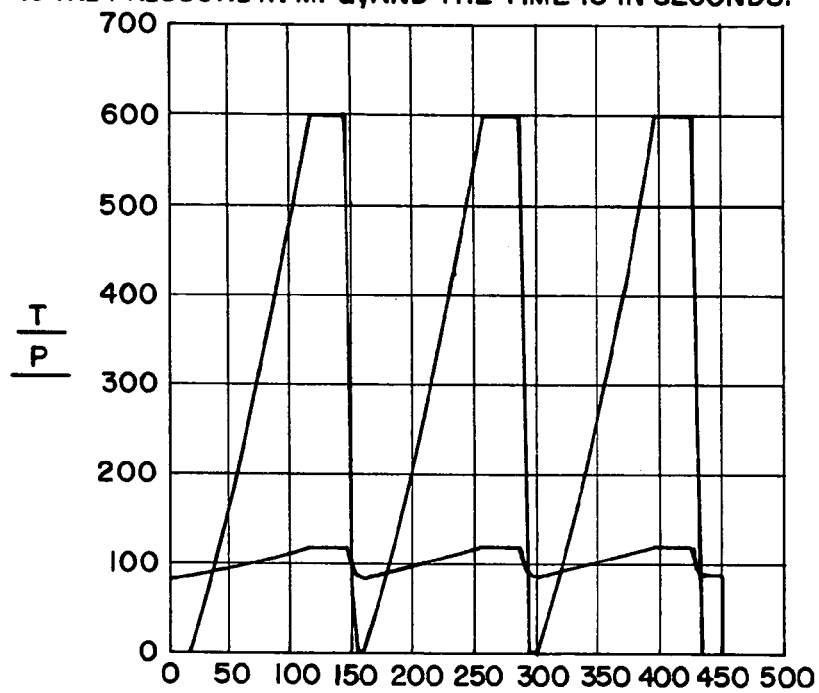

FIG.10

PARTICLE SIZE DISTRIBUTION OF THE 1% ITRACONAZOLE NANOSUSPENSION AFTER HIGH-PRESSURE AUTOCLAVING USING THE CYCLE SHOWN IN FIGURE 4.

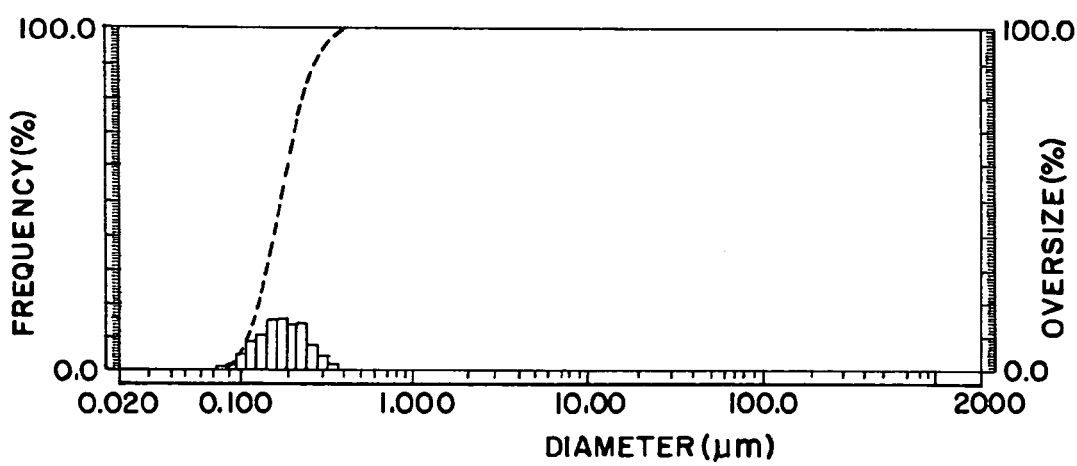

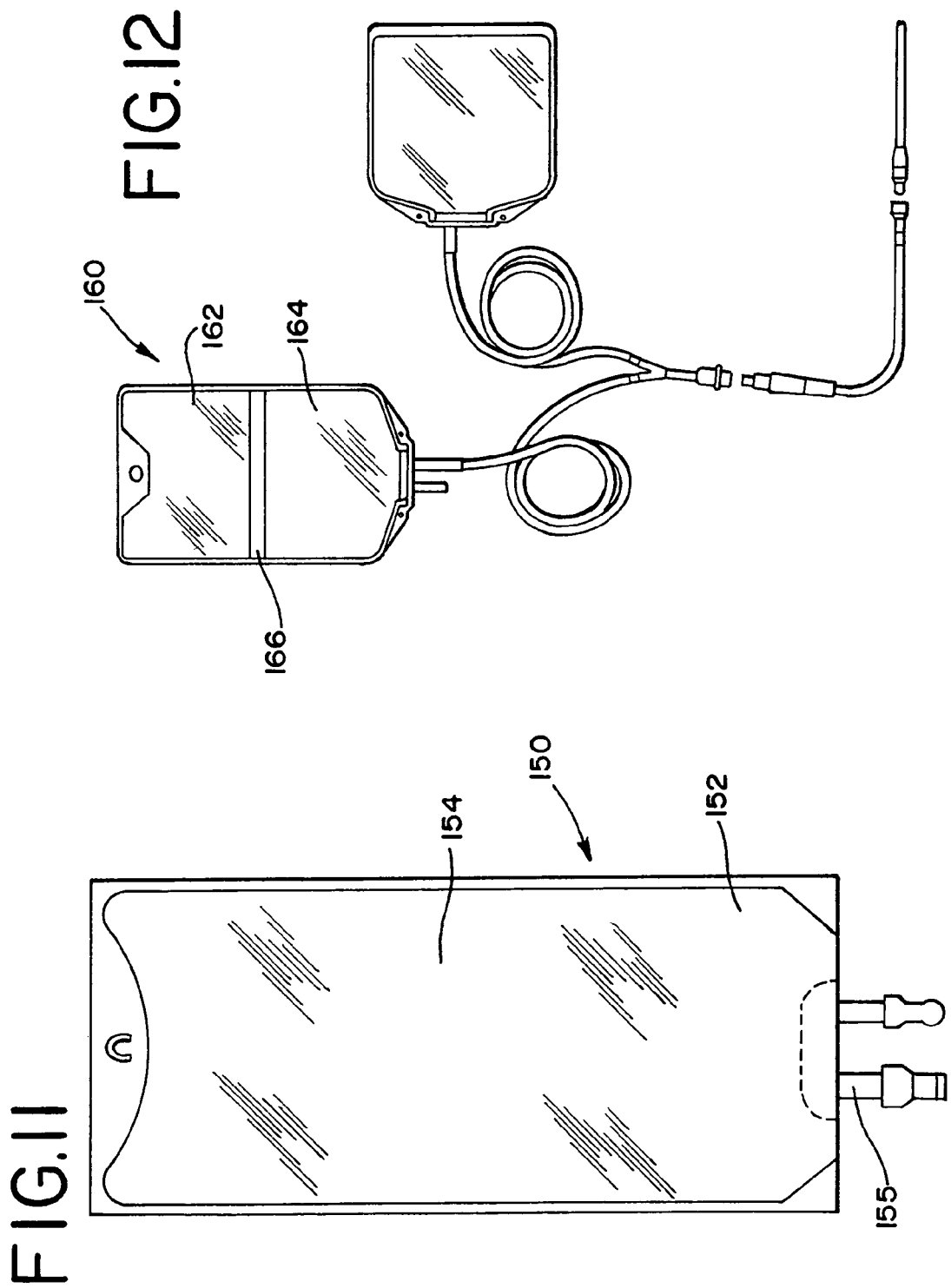

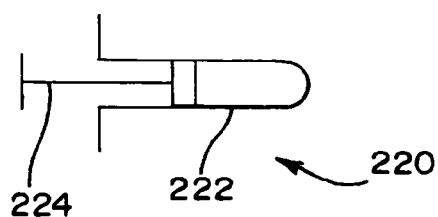
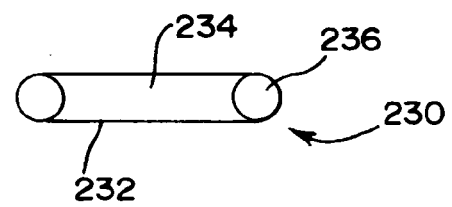
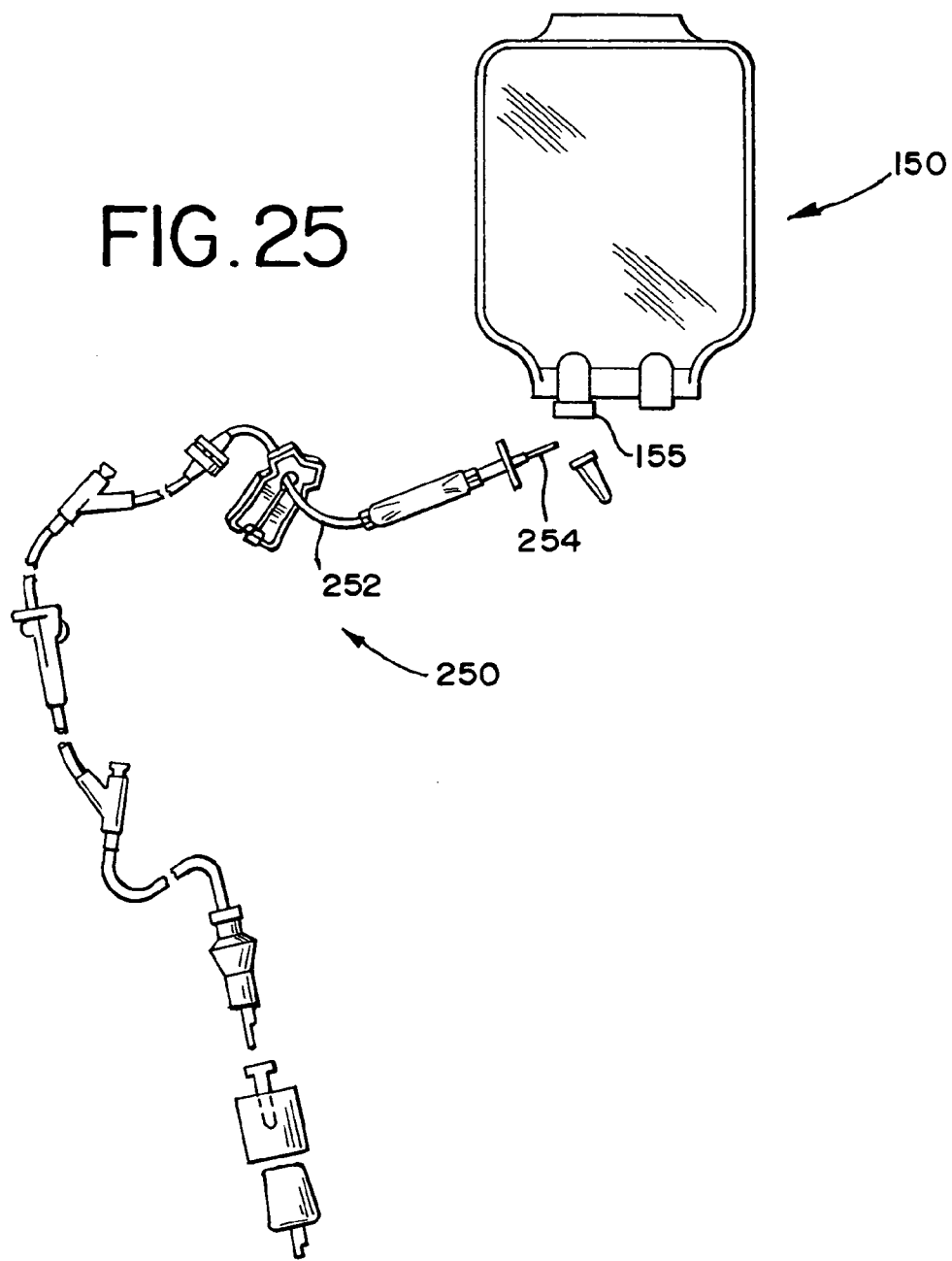

HIGH-PRESSURE STERILIZATION TO TERMINALLY STERILIZE PHARMACEUTICAL PREPARATIONS AND MEDICAL PRODUCTS

This application claims priority from provisional application No. 60/505,235, filed on Sep. 22, 2003.

BACKGROUND OF THE INVENTION

1. Technical Field

The present invention provides a process for sterilizing a pharmaceutical preparation such as a dispersion of small particles or droplets of a pharmaceutically active compound using high pressure terminal sterilization techniques and products therefrom.

2. Background of the Invention

There is an ever increasing number of organic compounds being formulated for therapeutic or diagnostic effects that are poorly soluble or insoluble in aqueous solutions. Such drugs provide challenges to delivering them by administrative routes commonly used by medical personnel. One potential solution to this challenge is to produce small particles of the insoluble drug candidate by preparing micro- or nanoparticulate dispersions therefrom. Benefits derived from such a formulation can include higher loading, reduced toxicity, improved drug saturation solubility and/or dissolution rate, improved efficacy, and enhanced drug stability.

In this way, drugs that were previously unable to be formulated in an aqueous based system can be made suitable for various routes of administration. Preparations of small particle dispersions of water insoluble drugs may be delivered via intraveneous, oral, pulmonary, topical, intrathecal, ophthalmic, nasal, buccal, rectal, vaginal, and transdermal routes. The optimum size range for these dispersions generally depends on the specific route, particle characteristics, and other factors, e.g., in intraveneous administration it is desirable to have a particle size of less than about 7 um. Particles must be in this size range and unaggregated to safely pass through capillaries without causing emboli (Allen et al., 1987; Davis and Taube, 1978; Schroeder et al., 1978; Yokel et al., 1981).

Depending on the route of administration and other factors, these small particle dispersions have to meet certain requirements of sterility. One useful sterilization method is conventional terminal autoclaving of small particle dispersions at 121° C. It is well known that pharmaceutical suspensions are protected from particle growth and/or aggregation during storage at normal temperatures by the presence of surfactants in the formulations. Even in the presence of these stabilizing surfactants, however, small particle suspensions are often quite heat-sensitive and cannot tolerate terminal autoclaving. The pharmaceutically active ingredient, surfactants, and the drug/surfactant assembly have to remain both physically and chemically stable during the entire sterilization cycle at 121° C. The chemical suspectibility of small particle dispersions to terminal autoclaving is known to be both a function of sterilization time and temperature. Methods for curtailing chemical instability generally involve high-temperature short-time sterilization processes. In this case, the preservation of the heat-labile formulation and destruction of microorganisms is based on the differences in rates of chemical degradation and inactivation, respectively. A significant challenge in this process is obtaining rapid enough heat transfer such that a uniform temperature exists throughout the product during the very short time of exposure.

The physical stability of the drug/surfactant assembly is also often difficult to maintain. The small particles frequently aggregate, grow, and/or degrade in the presence of the heat, rendering the final dispersion unusable. In addition, the surfactant assembly may dissociate from the pharmaceutically active compound in an irreversible fashion. For example, one mechanism of aggregation or coalescence of solid submicron particle dispersions can be directly related to precipitation of the stabilizing surfactant during the sterilization process, at temperatures above the surfactant's cloud point. The term "cloud point" refers to separation of an isotropic surfactant solution into one surfactant-rich and one surfactant-poor phase. At such temperatures, the surfactant often dissociates from the particle, causing the unprotected particles to aggregate and/or grow. Consequently, a number of patents (e.g., U.S. Pat. No. 5,298,262, U.S. Pat. No. 5,346,702, U.S. Pat. No. 5,470,583, U.S. Pat. No. 5,336,507) disclose using ionic and non-ionic cloud point modifiers to stabilize particle suspension during autoclaving. These modifiers raise the cloud point of the surfactant above 121° C., preventing the disassociation of the surfactant from the drug particle, and subsequently stabilize the particles from growth during terminal sterilization.

U.S. Pat. No. 6,267,989 also discloses that an optimal size range is most important to minimize growth and instability during autoclaving. The '989 patent reports that the highest stability is exhibited when at least 50% of the surfactant-stabilized drug particles have a weight average particle size between 150-350 nm.

Therefore, there is a continued need to develop new and improved processes for terminal sterilization of small particle dispersions in the pharmaceutical field, and the present invention addresses these needs.

Systems and solutions other that particulate dispersions often require sterilization prior to use. Examples include dissolved pharmaceutical solutions, solutions for renal application (e.g., peritoneal dialysis) and other forms of pharmaceutical preparations such as lipid emulsions. Other examples include medical device disposables, such as pharmaceutical-containing bags (often made of plasticized PVC or other plastics), blood-containing bags, dialyzers, systems for use on automated devices (e.g., blood separation devices, infusion pumps, etc.) Such systems may be sensitive to traditional sterilization techniques such as gamma sterilization, ETO sterilization or autoclaving. For example, glucose-containing solutions are subject to glucose breakdown or aggregation following traditional sterilization techniques. A need also exists, therefore, for the provision of improved sterilization techniques that provide adequate sterilization with little to no compromise of the system sterilized.

SUMMARY OF THE INVENTION

The present provides a method for sterilizing systems. Such systems can be, but are not limited to, compositions, such as particulate dispersions and devices, such as containers, which can contain aqueous solutions such as pharmaceutical preparations. The method has the advantage of providing for sterilization without significantly diminishing the efficacy of such systems. The invention further provides sterilized pharmaceutical preparations. Suitable containers include any container that is stabile under the present method including medical delivery devices containing medical solutions.

The method involves supplying heat energy to the system and pressurizing the system in excess of 0.25 MPa for a period of time sufficient to make the system sterile. Preferably, the system will achieve a temperature in excess of 70° C. The steps of supplying energy and pressure are carried out simultaneously for at least a sufficient period of time to sterilize the system. The system can then be allowed to return to ambient temperature and pressure for use.

The method can be used on empty containers or containers containing any of a wide variety of solutions including solutions for parenteral administration, solutions for acute or chronic hemodialysis, hemofiltration or hemodiafiltration solutions for acute or chronic peritoneal dialysis, ambulatory peritoneal dialysis and automated peritoneal dialysis.

The method is particularly useful in the sterilization of solutions that contain glucose. The lower temperature used for sterilization minimizes glucose degradation that occurs at higher temperatures. Thus, the method can be used to sterilize solutions containing glucose such that the glucose remains substantially undegraded. Preferably the glucose is over about 75% undegraded after sterilization, more preferably the glucose is over about 80% undegraded, still more preferred are sterilized solutions in which the glucose is more than about 85%, or more than about 90% or even more preferably more than about 95% undegraded.

These and other aspects and attributes of the present invention will be discussed with reference to the following drawings and accompanying specification.

BRIEF DESCRIPTION OF THE FIGURES

FIG. 9 shows a high-pressure sterilization cycle (Example 1);
FIG. 10 shows a particle size distribution curve;
FIG. 11 shows a flowable materials container;
FIG. 12 shows a multiple chamber peel seal container;
FIG. 23 shows a syringe;
FIG. 24 shows a cartridge for a medical delivery device;
and
FIG. 25 shows a fluid access device.

DETAILED DESCRIPTION OF THE INVENTION

Figure 1:
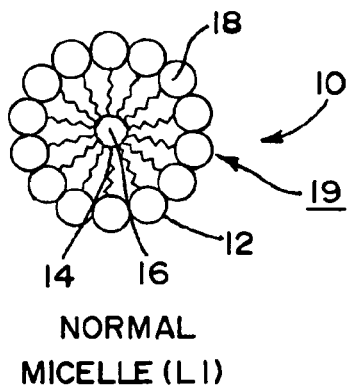
FIG. 1 shows a micelle.

While this invention is susceptible of embodiment in many different forms, there is shown in the drawing, and will be described herein in detail, specific embodiments thereof with the understanding that the present disclosure is to be considered as an exemplification of the principles of the invention and is not intended to limit the invention to the specific embodiments illustrated.

The present invention provides a method for sterilizing a system without significantly diminishing the usability, stability, and/or efficacy of the preparation. The present invention provides a method of sterilizing a dynamic system (i.e., a system capable of going from a stable to an unstable state) wherein the system is subjected to high pressure for a time sufficient to sterilize the system without causing the system to go from a stable state to an unstable state.

As used herein, the term "sterilization" and its variants shall mean the kill or control of bacteria, virus, protozoa or other biological microbes in a system such that the system provides a reduced risk of infection upon use with a mammal, preferably a human. Preferred methods of the present invention shall sterilize a system to the point that all or nearly all of the biological microbes are killed or rendered non-replicating.

Preferably, the method is used for sterilizing a pharmaceutical system. The pharmaceutical preparation can be prepared by numerous techniques known in the art and that will be developed. In general, the method provides subjecting a system to high-pressure sterilization. The method is preferred for high-pressure sterilization of small particle dispersions. The invention further provides sterilized pharmaceutical dispersions.

The high-pressure sterilization techniques of the present invention allow for sterilization of small particle dispersions without causing significant degradation of the pharmaceutically active compound, degradation of the surfactants, or causing a change to the drug/surfactant assembly. Moreover, heat is transferred instantaneously throughout the dispersion due to rapid adiabatic heating of the formulation during the compression step. It is anticipated that the high-pressure sterilization techniques are sutiable for use with many small particle dispersions containing various pharmaceutical compounds in a number of container configurations.

In general, the method provides subjecting a pharmaceutical preparation to high-pressure sterilization. The pharmaceutical preparation can be prepared by numerous techniques known in the art and that will be developed. The high-pressure sterilization techniques are well suited to sterilize formulations in many different forms including a pharmaceutically effective compound in a dry or powder form, liquid form, gas form or dispersed as small particles or droplets in an aqueous or organic media. Preferably, the system to be sterilized will contain some water. The presence of water has been shown to provide particular effectiveness in obtaining reduction in active microbe load. It is well known to stabilize pharmaceutically active compounds from aggregation and size changes using surfactants. The surfactants can be associated with the pharmaceutically active compound in one of many ways well known in the art. The high-pressure sterilization techniques of the present invention allow for sterilization without causing a degradation of the pharmaceutically active compound, or causing a significant disassociation of the surfactant from the pharmaceutically active compound. The method and products of this invention do not require the use of chemical cloud point modifiers. The term "cloud point" refers to an increase in turbidity of a pharmaceutical preparation when, a change in a physical property of the preparation such as a change in temperature or pH or other physical property, causes the surfactant to disassociate from the pharmaceutically active compound.

It is contemplated that the high-pressure sterilization techniques are suitable for use with a number of organic compounds.

I. Pharmaceutically Active Compounds

The method of the present invention is suitable for the sterilization of pharmaceutical preparations in general. In preferred methods of the present invention, the pharmaceutically active ingredient will be such that it associates with a dispersed hydrophobic region (e.g., surfactant assembled hydrophobic phase, cyclodextrin cavity, oil droplet) in aqueous solution. Pharmaceutically active compounds can be selected from therapeutic agents, renal therapy products, diagnostic agents, cosmetics, nutritional supplements, and pesticides.

The pharmaceutical active agents can be selected from a variety of known classes such as, but are not limited to: analgesics, anesthetics, analeptics, adrenergic agents, adrenergic blocking agents, adrenolytics, adrenocorticoids, adrenomimetics, anticholinergic agents, anticholinesterases, anticonvulsants, alkylating agents, alkaloids, allosteric inhibitors, anabolic steroids, anorexiants, antacids, antidiarrheals, antidotes, antifolics, antipyretics, antirheumatic agents, psychotherapeutic agents, neural blocking agents, anti-inflammatory agents, antihelmintics, anti-arrhythmic agents, antibiotics, anticoagulants, antidepressants, antidiabetic agents, antiepileptics, antifungals, antihistamines, antihypertensive agents, antimuscarinic agents, antimycobacterial agents, antimalarials, antiseptics, antineoplastic agents, antiprotozoal agents, immunosuppressants, immunostimulants, antithyroid agents, antiviral agents, anxiolytic sedatives, astringents, beta-adrenoceptor blocking agents, contrast media, corticosteroids, cough suppressants, diagnostic agents, diagnostic imaging agents, diuretics, dopaminergics, hemostatics, hematological agents, hemoglobin modifiers, hormones, hypnotics, immuriological agents, antihyperlipidemic and other lipid regulating agents, muscarinics, muscle relaxants, parasympathomimetics, parathyroid calcitonin, prostaglandins, radio-pharmaceuticals, sedatives, sex hormones, anti-allergic agents, stimulants, sympathomimetics, thyroid agents, vasodilators, vaccines, vitamins, and xanthines. Antineoplastic, or anticancer agents, include but are not limited to paclitaxel and derivative compounds, and other antineoplastics selected from the group consisting of alkaloids, antimetabolites, enzyme inhibitors, alkylating agents and antibiotics. The therapeutic agent can also be a biologic, which includes but is not limited to proteins, polypeptides, carbohydrates, polynucleotides, and nucleic acids. The protein can be an antibody, which can be polyclonal or monoclonal.

Diagnostic agents include the x-ray imaging agents and contrast media. Examples of x-ray imaging agents include WIN-8883 (ethyl 3,5-diacetamido-2,4,6-triiodobenzoate) also known as the ethyl ester of diatrazoic acid (EEDA), WIN 67722, i.e., (6-ethoxy-6-oxohexyl-3,5-bis(acetamido)-2,4,6-triiodobenzoate; ethyl-2-(3,5-bis(acetamido)-2,4,6-triiodobenzoyloxy) butyrate (WIN 16318); ethyl diatrizoxyacetate (WIN 12901); ethyl 2-(3,5-bis(acetamido)-2,4,6-triiodobenzoyloxy)propionate (WIN 16923); N-ethyl 2-(3,5-bis(acetamido)-2,4,6-triiodobenzoyloxy acetamide (WIN 65312); isopropyl 2-(3,5-bis(acetamido)-2,4,6-triiodobenzoyloxy) acetamide (WIN 12855); diethyl 2-(3,5-bis(acetamido)-2,4,6-triiodobenzoyloxy malonate (WIN 67721); ethyl 2-(3,5-bis (acetamido)-2,4,6-triiodobenzoyloxy) phenylacetate (WIN 67585); propanedioic acid, [[3,5-bis(acetylamino)-2,4,5-triodobenzoyl]oxy]bis(1-methyl)ester (WIN 68165); and benzoic acid, 3,5-bis(acetylamino)-2,4,6-triodo-4-(ethyl-3-ethoxy-2-butenoate) ester (WIN 68209). Preferred contrast agents include those that are expected to disintegrate relatively rapidly under physiological conditions, thus minimizing any particle associated inflammatory response. Disintegration may result from enzymatic hydrolysis, solubilization of carboxylic acids at physiological pH, or other mechanisms. Thus, poorly soluble iodinated carboxylic acids such as iodipamide, diatrizoic acid, and metrizoic acid, along with hydrolytically labile iodinated species such as WIN 67721, WIN 12901, WIN 68165, and WIN 68209 or others may be preferred.

Other contrast media include, but are not limited to, particulate preparations of magnetic resonance imaging aids such as gadolinium chelates, or other paramagnetic contrast agents. Examples of such compounds are gadopentetate dimeglumine (Magnevist®) and gadoteridol (Prohance®).

A description of these classes of therapeutic agents and diagnostic agents and a listing of species within each class can be found in Martindale, The Extra Pharmacopoeia, Twenty-ninth Edition, The Pharmaceutical Press, London, 1989, which is incorporated herein by reference and made a part hereof. The therapeutic agents and diagnostic agents are commercially available and/or can be prepared by techniques known in the art.

Renal therapeutic agents include solutions for continuous ambulatory dialysis, automated peritoneal dialysis and hemodialysis.

A cosmetic agent is any active ingredient capable of having a cosmetic activity. Examples of these active ingredients can be, inter alia, emollients, humectants, free radical-inhibiting agents, anti-inflammatories, vitamins, depigmenting agents, anti-acne agents, antiseborrhoeics, keratolytics, slimming agents, skin coloring agents and sunscreen agents, and in particular linoleic acid, retinol, retinoic acid, ascorbic acid alkyl esters, polyunsaturated fatty acids, nicotinic esters, tocopherol nicotinate, unsaponifiables of rice, soybean or shea, ceramides, hydroxy acids such as glycolic acid, selenium derivatives, antioxidants, beta-carotene, gamma-orizanol and stearyl glycerate. The cosmetics are commercially available and/or can be prepared by techniques known in the art.

Examples of nutritional supplements contemplated for use in the practice of the present invention include, but are not limited to, proteins, carbohydrates, water-soluble vitamins (e.g., vitamin C, B-complex vitamins, and the like), fat-soluble vitamins (e.g., vitamins A, D, E, K, and the like), and herbal extracts. The nutritional supplements are commercially available and/or can be prepared by techniques known in the art.

The term pesticide is understood to encompass herbicides, insecticides, acaricides, nematicides, ectoparasiticides and fungicides. Examples of compound classes to which the pesticide in the present invention may belong include ureas, triazines, triazoles, carbamates, phosphoric acid esters, dinitroanilines, morpholines, acylalanines, pyrethroids, benzilic acid esters, diphenylethers and polycyclic halogenated hydrocarbons. Specific examples of pesticides in each of these classes are listed in Pesticide Manual, 9th Edition, British Crop Protection Council. The pesticides are commercially available and/or can be prepared by techniques known in the art.

Preferably the pharmaceutically active compound is poorly water-soluble. What is meant by "poorly water soluble" is a solubility of the compound in water of less than about 10 mg/mL, and preferably less than 1 mg/mL. These poorly water-soluble agents are most suitable for aqueous suspension preparations since there are limited alternatives of formulating these agents in an aqueous medium.

The present invention can also be practiced with water-soluble pharmaceutically active compounds in certain cases, by entrapping these compounds in a solid hydrophobic dispersed phase (e.g., in polylactate-polyglycolate copolymer or solid lipid nanoparticles), or by encapsulating these compounds in a surrounding surfactant assembly that is impermeable to the pharmaceutical compound. Examples of surfactant assemblies include, but are not limited to, vesicles and micelles. Examples of water-soluble pharmaceutical agents include, but are not limited to, simple organic compounds, proteins, peptides, nucleotides, oligonucleotides, and carbohydrates.

II. Particle Size of the Dispersion and Routes of Administration

When the pharmaceutical agents of the present invention are in particle form (i.e., not dissolved in solvent), the particles will have an average effective particle size of generally less than about 100 µm as measured by dynamic light scattering methods, e.g., photocorrelation spectroscopy, laser diffraction, low-angle laser light scattering (LALLS), medium-angle laser light scattering (MALLS), light obscuration methods (Coulter method, for example), rheology, or microscopy (light or electron). However, the particles can be prepared in a wide range of sizes, such as from about 100 µm to about 10 nm, from about 10 µm to about 10 nm, from about 2 µm to about 10 nm, from about 1 µm to about 10 nm, from about 400 nm to about 50 nm, from about 200 nm to about 50 nm or any range or combination of ranges therein. The preferred average effective particle size depends on factors such as the intended route of administration, formulation, solubility, toxicity and bioavailability of the compound.

To be suitable for parenteral administration, the particles preferably have an average effective particle size of less than about 7 µm, and more preferably less than about 2 µm or any range or combination of ranges therein. Parenteral administration includes intravenous, intra-arterial, intrathecal, intraperitoneal, intraocular, intra-articular, intradural, intraventricular, intrapericardial, intramuscular, intradermal or subcutaneous injection.

Particles sizes for oral dosage forms can be in excess of 2 µm. The particles can range in size up to about 100 µm, provided that the particles have sufficient bioavailability and other characteristics of an oral dosage form. Oral dosage forms include tablets, capsules, caplets, soft and hard gel capsules, or other delivery vehicle for delivering a drug by oral administration.

The present invention is further suitable for providing particles of the pharmaceutically active compound in a form suitable for pulmonary administration. Particles sizes for pulmonary dosage forms can be in excess of 500 nm and typically less than about 10 µm. The particles in the suspension can be aerosolized and administered by a nebulizer for pulmonary administration. Alternatively, the particles can be administered as dry powder by a dry powder inhaler after removing the liquid phase from the suspension, or the dry powder can be resuspended in a non-aqueous propellant for administration by a metered dose inhaler. An example of a suitable propellant is a hydrofluorocarbon (HFC) such as HFC-134a (1,1,1,2-tetrafluoroethane) and HFC-227ea (1,1,1,2,3,3,3-heptafluoropropane). Unlike chlorofluorcarbons (CFC's), HFC's exhibit little or no ozone depletion potential.

We will collectively refer to particles and droplets of the organic compounds from the size ranges set forth above as small particles.

Dosage forms for other routes of delivery, such as nasal, topical, ophthalmic, nasal, buccal, rectal, vaginal, transdermal and the like can also be formulated from the particles made from the present invention.

Other forms of solutions can be sterilized by the present invention. Examples of such solutions include pharmaceutical preparation for parenteral administration and solutions for renal dialysis, such as hemodialysis and peritoneal dialysis solutions.

III. Preparation of Small Particle Dispersions

There are numerous techniques for preparing pharmaceutical preparations of small particles of pharmaceutically active compounds. The sterilization techniques discussed below are suitable for sterilizing such pharmaceutical preparations. Representative, though not exhaustive, examples of methodologies for providing small particles of pharmaceutically active compounds are briefly discussed next.

A. Energy Addition Techniques for Forming Small Particle Dispersions

In general, the method of preparing small particle dispersions using energy addition techniques includes the step of adding the pharmaceutically active compound, which sometimes shall be referred to as a drug, in bulk form to a suitable vehicle such as water or aqueous based solution containing one or more of the surfactants set forth below, or other liquid in which the pharmaceutical compound is not appreciably soluble, to form a presuspension. Energy is added to the presuspension to form a particle dispersion. Energy is added by mechanical grinding, pearl milling, ball milling, hammer milling, fluid energy milling or wet grinding. Such techniques are disclosed in U.S. Pat. No. 5,145,684, which is incorporated herein by reference and made a part hereof.

Energy addition techniques further include subjecting the presuspension to high shear conditions including cavitation, shearing or impact forces utilizing a microfluidizer. The present invention further contemplates adding energy to the presuspension using a piston gap homogenizer or counter current flow homogenizer such as those disclosed in U.S. Pat. No. 5,091,188 which is incorporated herein by reference and made a part hereof. Suitable piston gap homogenizers are commercially available under the product name EMULSIFLEX by Avestin, and French Pressure Cells sold by Spectronic Instruments. Suitable microfluidizers are available from Microfluidics Corp.

The step of adding energy can also be accomplished using sonication techniques. The step of sonicating can be carried out with any suitable sonication device such as the Branson Model S-450A or Cole-Parmer 500/750 Watt Model. Such devices are well known in the industry. Typically the sonication device has a sonication horn or probe that is inserted into the presuspension to emit sonic energy into the solution. The sonicating device, in a preferred form of the invention, is operated at a frequency of from about 1 kHz to about 90 kHz and more preferably from about 20 kHz to about 40 kHz or any range or combination of ranges therein. The probe sizes can vary and preferably is in distinct sizes such as ½ inch or ¼ inch or the like.

Regardless of the energy addition technique used, the dispersion of small particles needs to meet appropriate sterility assurance levels before use. Sterilization can be accomplished using the high-pressure sterilization techniques described below.

B. Precipitation Methods for Preparing Submicron Sized Particle Dispersions

Small particle dispersions can also be prepared by well-known precipitation techniques. The following are precipitation techniques used to produce solid submicron dispersions.

Microprecipitation Methods

One example of a microprecipitation method is disclosed in U.S. Pat. No. 5,780,062, which is incorporated herein by reference and made a part hereof. The '062 patent discloses an organic compound precipitation process including: (i) dissolving the organic compound in a water-miscible first solvent; (ii) preparing a solution of polymer and an amphiphile in an aqueous second solvent and in which second solvent the organic compound is substantially insoluble whereby a polymer/amphiphile complex is formed; and (iii) mixing the solutions from steps (i) and (ii) so as to cause precipitation of an aggregate of the organic compound and the polymer/amphiphile complex.

Another example of a suitable precipitation process is disclosed in co-pending and commonly assigned U.S. Ser. Nos. 09/874,499; 09/874,799; 09/874,637; and 10/021,692, which are incorporated herein by reference and made a part hereof. The processes disclosed include the steps of: (1) dissolving an organic compound in a water miscible first organic solvent to create a first solution; (2) mixing the first solution with a second solvent or water to precipitate the organic compound to create a presuspension; and (3) adding energy to the presuspension in the form of high-shear mixing or heat to provide a dispersion of small particles. One or more optional surface modifiers set forth below can be added to the first organic solvent or the second aqueous solution.

Emulsion Precipitation Methods

One suitable emulsion precipitation technique is disclosed in the co-pending and commonly assigned U.S. Ser. No. 09/964,273, which is incorporated herein by reference and is made a part hereof. In this approach, the process includes the steps of: (1) providing a multiphase system having an organic phase and an aqueous phase, the organic phase having a pharmaceutically active compound therein; and (2) sonicating the system to evaporate a portion of the organic phase to cause precipitation of the compound in the aqueous phase to form a dispersion of small particles. The step of providing a multiphase system includes the steps of: (1) mixing a water immiscible solvent with the pharmaceutically active compound to define an organic solution, (2) preparing an aqueous based solution with one or more surface active compounds, and (3) mixing the organic solution with the aqueous solution to form the multiphase system. The step of mixing the organic phase and the aqueous phase can include the use of piston gap homogenizers, colloidal mills, high speed stirring equipment, extrusion equipment, manual agitation or shaking equipment, microfluidizer, or other equipment or techniques for providing high shear conditions. The crude emulsion will have oil droplets in the water of a size of approximately less than 1 µm in diameter. The crude emulsion is sonicated to define a finer emulsion and eventually to provide a dispersion of small particles.

Another approach to preparing a dispersion of small particles is disclosed in co-pending and commonly assigned U.S. Ser. No. 10/183,035, which is incorporated herein by reference and made a part hereof. The process includes the steps of: (1) providing a crude dispersion of a multiphase system having an organic phase and an aqueous phase, the organic phase having a pharmaceutical compound therein; (2) providing energy to the crude dispersion to form a fine dispersion; (3) freezing the fine dispersion; and (4) lyophilizing the fine dispersion to obtain small particles of the pharmaceutical compound. The small particles can be sterilized by the techniques set forth below or the small particles can be reconstituted in an aqueous medium and sterilized.

The step of providing a multiphase system includes the steps of: (1) mixing a water immiscible solvent with the pharmaceutically effective compound to define an organic solution; (2) preparing an aqueous based solution with one or more surface active compounds; and (3) mixing the organic solution with the aqueous solution to form the multiphase system. The step of mixing the organic phase and the aqueous phase includes the use of piston gap homogenizers, colloidal mills, high speed stirring equipment, extrusion equipment, manual agitation or shaking equipment, microfluidizer, or other equipment or techniques for providing high shear conditions.

Solvent Anti-Solvent Precipitation

Small particle dispersions can also be prepared using solvent anti-solvent precipitation technique disclosed in U.S. Pat. Nos. 5,118,528 and 5,100,591 which are incorporated herein by reference and made a part hereof. The process includes the steps of: (1) preparing a liquid phase of a biologically active substance in a solvent or a mixture of solvents to which may be added one or more surfactants; (2) preparing a second liquid phase of a non-solvent or a mixture of non-solvents, the non-solvent is miscible with the solvent or mixture of solvents for the substance; (3) adding together the solutions of (1) and (2) with stirring; and (4) removing of unwanted solvents to produce a dispersion of small particles Phase Inversion Precipitation Small particle dispersions can be formed using phase inversion precipitation as disclosed in U.S. Pat. Nos. 6,235,224, 6,143,211 and U.S. patent application No. 2001/0042932 each of which is incorporated herein by reference and made a part hereof. Phase inversion is a term used to describe the physical phenomena by which a polymer dissolved in a continuous phase solvent system inverts into a solid macromolecular network in which the polymer is the continuous phase. One method to induce phase inversion is by the addition of a nonsolvent to the continuous phase. The polymer undergoes a transition from a single phase to an unstable two-phase mixture: polymer rich and polymer poor fractions. Micellar droplets of nonsolvent in the polymer rich phase serve as nucleation sites and become coated with polymer. The '224 patent discloses that phase inversion of polymer solutions under certain conditions can bring about spontaneous formation of discrete microparticles, including nanoparticles. The '224 patent discloses dissolving or dispersing a polymer in a solvent. A pharmaceutical agent is also dissolved or dispersed in the solvent. The polymer, the agent and the solvent together form a mixture having a continuous phase, wherein the solvent is the continuous phase. The mixture is then introduced into at least tenfold excess of a miscible nonsolvent to cause the spontaneous formation of the microencapsulated microparticles of the agent having an average particle size of between 10 nm and 10 µm. The particle size is influenced by the solvent:nonsolvent volume ratio, polymer concentration, the viscosity of the polymer-solvent solution, the molecular weight of the polymer, and the characteristics of the solvent-nonsolvent pair.

pH Shift Precipitation

Small particle dispersions can be formed by pH shift precipitation techniques. Such techniques typically include a step of dissolving a drug in a solution having a pH where the drug is soluble, followed by the step of changing the pH to a point where the drug is no longer soluble. The pH can be acidic or basic, depending on the particular pharmaceutical compound. The solution is then neutralized to form a dispersion of small particles. One suitable pH shifting precipitation process is disclosed in U.S. Pat. No. 5,665,331, which is incorporated herein by reference and made a part hereof. The process includes the step of dissolving of the pharmaceutical agent together with a crystal growth modifier (CGM) in an alkaline solution and then neutralizing the solution with an acid in the presence of suitable surface-modifying surface-active agent or agents to form a small particle dispersion of the pharmaceutical agent. The precipitation step can be followed by steps of diafiltration and purification of the dispersion followed by adjusting the concentration of the dispersion to a desired level.

Other examples of pH shifting precipitation methods are disclosed in U.S. Pat. Nos. 5,716,642; 5,662,883; 5,560,932; and 4,608,278, which are incorporated herein by reference and are made a part hereof.

Infusion Precipitation Method

Suitable infusion precipitation techniques to form small particle dispersions are disclosed in the U.S. Pat. Nos. 4,997,454 and 4,826,689, which are incorporated herein by reference and made a part hereof. First, a suitable solid compound is dissolved in a suitable organic solvent to form a solvent mixture. Then, a precipitating nonsolvent miscible with the organic solvent is infused into the solvent mixture at a temperature between about −10° C. and about 100° C. and at an infusion rate of from about 0.01 ml per minute to about 1000 ml per minute per volume of 50 ml to produce a suspension of precipitated non-aggregated solid particles of the compound with a substantially uniform mean diameter of less than 10 µm. Agitation (e.g., by stirring) of the solution being infused with the precipitating nonsolvent is preferred. The nonsolvent may contain a surfactant to stabilize the particles against aggregation. The particles are then separated from the solvent. Depending on the solid compound and the desired particle size, the parameters of temperature, ratio of nonsolvent to solvent, infusion rate, stir rate, and volume can be varied according to the invention. The particle size is proportional to the ratio of nonsolvent:solvent volumes and the temperature of infusion and is inversely proportional to the infusion rate and the stirring rate. The precipitating nonsolvent may be aqueous or non-aqueous, depending upon the relative solubility of the compound and the desired suspending vehicle.

Temperature Shift Precipitation

Temperature shift precipitation techniques may also be used to form small particle dispersions. This technique is disclosed in U.S. Pat. No. 5,188,837, which is incorporated herein by reference and made a part hereof. In an embodiment of the invention, liposheres are prepared by the steps of: (1) melting or dissolving a substance such as a drug to be delivered in a molten vehicle to form a liquid of the substance to be delivered; (2) adding a phospholipid along with an aqueous medium to the melted substance or vehicle at a temperature higher than the melting temperature of the substance or vehicle; (3) mixing the suspension at a temperature above the melting temperature of the vehicle until a homogenous fine preparation is obtained; and then (4) rapidly cooling the preparation to room temperature or below.

Solvent Evaporation Precipitation

Solvent evaporation precipitation techniques are disclosed in U.S. Pat. No. 4,973,465 which is incorporated herein by reference and made a part hereof. The '465 patent discloses methods for preparing microcrystals including the steps of: (1) providing a solution of a pharmaceutical composition and a phospholipid dissolved in a common organic solvent or combination of solvents, (2) evaporating the solvent or solvents and (3) suspending the film obtained by evaporation of the solvent or solvents in an aqueous solution by vigorous stirring to form a dispersion of small particles. The solvent can be removed by adding energy to the solution to evaporate a sufficient quantity of the solvent to cause precipitation of the compound. The solvent can also be removed by other well-known techniques such as applying a vacuum to the solution or blowing nitrogen over the solution.

Reaction Precipitation

Reaction precipitation includes the steps of dissolving the pharmaceutical compound into a suitable solvent to form a solution. The compound should be added in an amount at or below the saturation point of the compound in the solvent. The compound is modified by reacting with a chemical agent or by modification in response to adding energy such as heat or UV light or the like such that the modified compound has a lower solubility in the solvent and precipitates from the solution to form small particles.

Compressed Fluid Precipitation.

A suitable technique for precipitating by compressed fluid is disclosed in WO 97/14407 to Johnston, which is incorporated herein by reference and made a part hereof. The method includes the steps of dissolving a water-insoluble drug in a solvent to form a solution. The solution is then sprayed into a compressed fluid, which can be a gas, liquid or supercritical fluid. The addition of the compressed fluid to a solution of a solute in a solvent causes the solute to attain or approach supersaturated state and to precipitate out as fine particles. In this case, the compressed fluid acts as an anti-solvent which lowers the cohesive energy density of the solvent in which the drug is dissolved.

Alternatively, the drug can be dissolved in the compressed fluid which is then sprayed into an aqueous phase. The rapid expansion of the compressed fluid reduces the solvent power of the fluid, which in turn causes the solute to precipitate out as small particles in the aqueous phase. In this case, the compressed fluid acts as a solvent.

In order to stabilize the particles against aggregation, a surface modifier, such as a surfactant, is included in this technique.

There are numerous other methodologies for preparing small particle dispersions. The present invention provides a methodology for terminally sterilizing such dispersions without significantly impacting the efficacy of the preparation.

IV. Small Particle Dispersion Types

A small particle dispersion can be created from a hydrophobic region in the aqueous system (e.g. surfactant assembly, cyclodextrin cavity, oil droplet) and the pharmaceutically active compound, or from the hydrophobic region itself if it is pharmaceutically active. The hydrophobic region can associate with the pharmaceutically active compound by a number of different mechanisms in the small particle dispersion. For example, the hydrophobic region can be associated with the pharmaceutically active compound via a covalent bond, and ionic bond, dipole-dipole interactions, induced dipole-dipole interactions, or Van Der Waals forces. In addition, the pharmaceutically active compound can be encapsulated in the hydrophobic region.

A. Hydrophobic Regions

Surfactant Assemblies

Hydrophobic regions are known to form in aqueous solution from single or combinations of amphiphilic-type surfactants in aqueous solution (e.g., phospholipids). Surfactant assemblies include micelles (FIG. 1), reversed micelles (FIG. 2), mixed micelles, reversed mixed micelles, lamellar form (FIG. 3), reversed lamellar form, hexagonal phase (FIG. 4), reversed hexagonal phase, cubic phases (FIG. 5), reversed cubic phases, L3 sponge phases, reverse L3 sponge phases, and intermediate phases. The formation of normal or reverse phases depends on the surfactant type, surfactant concentration, pressure, and temperature. Cochelates would also fall within this class.

FIG. 1 shows a micelle 10 having numerous amphiphilic molecules 12 circumferentially spaced from one another and having the non-polar, hydrophobic, tails 14 of the amphiphilic molecules extending axially inwardly defining a core 16 and the polar, hydrophilic, headgroups 18 extending radially away from the core to define a surface 19.

Figure 2:
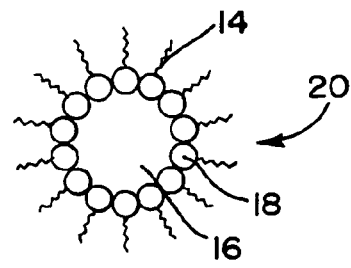
FIG. 2 shows a reversed micelle.

FIG. 2 shows a reverse micelle 20 which is the same in all respects to the micelle of FIG. 1 except the polar headgroups 18 extend inwardly toward the core and the non-polar tails extend outwardly away from the core. This will be true for the phases in general and their reverse counterparts. Thus, a figure for each reverse form has been omitted.

Figure 3:
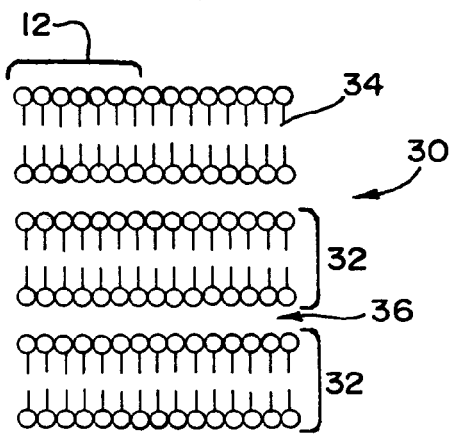
FIG. 3 shows a lamellar phase.

FIG. 3 shows a lamellar phase 30. The lamellar phase 30 has spaced amphiphilic molecules 12 forming stacked bi-layer structures 32. The area between the bi-layer structures 32 and the area between the hydrophobic tails are known as the pallisade layers 34 and 36. The pallisade layer 34 is hydrophobic and the pallisade layer 36 is bydrophylic.

Figure 4:
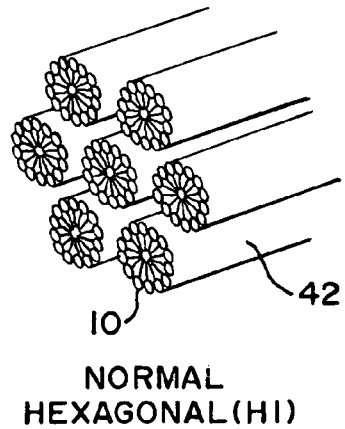
FIG. 4 shows a hexagonal phase.

FIG. 4 shows the hexagonal phase 40. The hexagonal phase can be envisioned as a series of normal micelles (FIG. 1) stacked on top of one another to form tube like structures 42.

Figure 5:
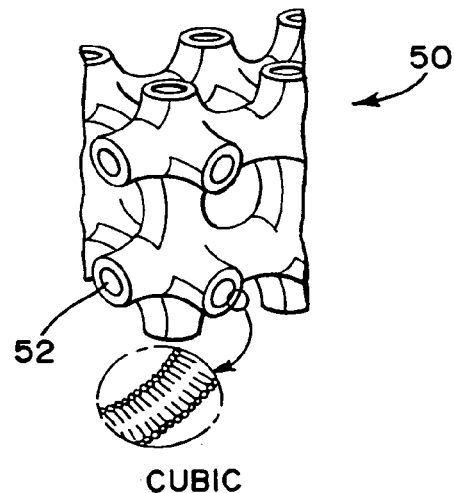
FIG. 5 shows a cubic phase.

FIG. 5 shows one example of a cubic phase 50. Seven cubic phases have been identified to date and the structure tentatively described. The bicontinuous cubic phase 50 has a series of bi-layer structures 32 which define an interconnected network of intersecting tubes providing aqueous pores 52.

The L3 phase is described in U.S. Pat. No. 5,531,925 which is incorporated herein by reference and made a part hereof. The L3 phase is very similar to the cubic phases, but lacking the long-range order of the cubic phase.

Complexing Agents

Hydrophobic regions can also be formed in aqueous solution by the addition of complexing agents, such as cyclodextrins. Cyclodextrins are also commonly used to interact with an insoluble drug compound in an aqueous solution as disclosed in U.S. Pat. No. 4,764,604 which is incorporated herein by reference and made a part hereof.

Two-Phase Dispersions

Hydrophobic regions in an aqueous system can also be formed from a number of heterogeneous two-phase systems, including emulsions, microemulsions, suspensions, as well as others.

As mentioned earlier, the present invention can be practiced with any of these formulations where the pharmaceutically active compound associates with the hydrophobic region to form a small particle dispersion, or from the hydrophobic region itself if it is pharmaceutically active. The pharmaceutically active compound can be incorporated into the hydrophobic region any of these types of formulations by the numerous mechanisms mentioned above. Many of these systems are described in detail in "Surfactants and Polymers in Aqueous Solution," 2003, John Wiley and Sons, which is incorporated herein by reference and made a part hereof.

V. Surfactants

Particularly important and safe classes of amphiphilic surfactants include phospholipids. Phospholipids typically are triglycerol derivatives having two hydroxyl groups of the glycerol ester linked to fatty acids (defining a polar tail) and one terminal hydroxyl group is linked to phosphoric acid. The phosphoric acid in turn is linked to another compound (e.g. choline, ethanolamine, ethylamine, glycerol, or L-serine) to define a polar head group. Suitable phospholipids include, for example phosphatidylcholine, phosphatidylethanolamine, phosphatidylserine, phosphatidylinositol, phosphatidylglycerol, phosphatidic acid, lysophospholipids, egg or soybean phospholipid or a combination thereof. The phospholipid may be salted or desalted, hydrogenated or partially hydrogenated or natural semisynthetic or synthetic.

Suitable surfactants of the present invention include anionic surfactants, cationic surfactants, nonionic surfactants, zwitterionic surfactants, or biological surface-active molecules. Suitable anionic and zwitterionic surfactants include but are not limited to potassium laurate, sodium lauryl sulfate, sodium dodecylsulfate, alkyl polyoxyethylene sulfates, sodium alginate, dioctyl sodium sulfosuccinate, glyceryl esters, sodium carboxymethylcellulose, cholic acid and other bile acids (e.g., cholic acid, deoxycholic acid, glycocholic acid, taurocholic acid, glycodeoxycholic acid) and salts thereof (e.g., sodium-deoxycholate, etc.). Suitable cationic surfactants include but are not limited to quaternary ammonium compounds, such as benzalkonium chloride, cetyltrimethylammonium bromide, lauryldimethylbenzylammonium chloride, acyl carnitine hydrochlorides, or alkyl pyridinium halides.

Suitable nonionic surfactants include: polyoxyethylene fatty alcohol ethers (Macrogol and Brij), polyoxyethylene sorbitan fatty acid esters (polysorbates), polyoxyethylene fatty acid esters (Myrj), sorbitan esters (Span), glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers (poloxamers), polaxamines, methylcellulose, hydroxycellulose, hydroxy propylcellulose, hydroxy propylmethylcellulose, noncrystalline cellulose, polysaccharides including starch and starch derivatives such as hydroxyethylstarch (HES), polyvinyl alcohol, and polyvinylpyrrolidone. In one preferred form of the invention, the nonionic surfactant is a polyoxyethylene and polyoxypropylene copolymer and preferably a block copolymer of propylene glycol and ethylene glycol. Such polymers are sold under the tradename POLOXAMER also sometimes referred to as PLURONIC®, and sold by several suppliers including BASF, Spectrum Chemical, and Ruger. Among polyoxyethylene fatty acid esters is included those having short alkyl chains. One example of such a surfactant is SOLUTOL® HS 15, polyethylene-660-hydroxystearate, manufactured by BASF Aktiengesellschaft.

Surface-active biological molecules include such molecules as albumin, casein, heparin, hirudin or other appropriate proteins.

For oral dosage forms one or more of the following excipients may be utilized: gelatin, casein, lecithin (phosphatides), gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens™, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol (PVA), and polyvinylpyrrolidone (PVP). Most of these excipients are described in detail in the Handbook of Pharmaceutical Excipients, published jointly by the American Pharmaceutical Association and The Pharmaceutical Society of Great Britain, the Pharmaceutical Press, 1986. The surface modifiers are commercially available and/or can be prepared by techniques known in the art. Two or more surface modifiers can be used in combination.

VI. Stabilization Effects of High Pressure on Small Particle Dispersions

High pressure can stabilize small particle systems by a number of different mechanisms, which can either be thermodynamic (volume of reaction) or kinetic (volume of activation) in origin. In addition, high pressure can chemically and/or physically stabilize the pharmaceutically active ingredient, surfactants, and/or the drug/hydrophobic region association during the entire sterilization cycle. An example of thermodynamic stabilization is the effect of high pressure on the cloud point of polyoxyethylene surfactants. For these systems, cloud points are known to rise on compression due to hydrogen bind enhancement and disruption of hydrophobic bonding. Consequently, small particle dispersions that are unstable during autoclaving due to cloud point precipitation can be stabilized by performing terminal sterilization at higher pressures such that the cloud point of the surfactant system is greater than 121° C.

Example 1

High-Pressure Sterilization of an Itraconazole Nanosuspension

Figure 7:
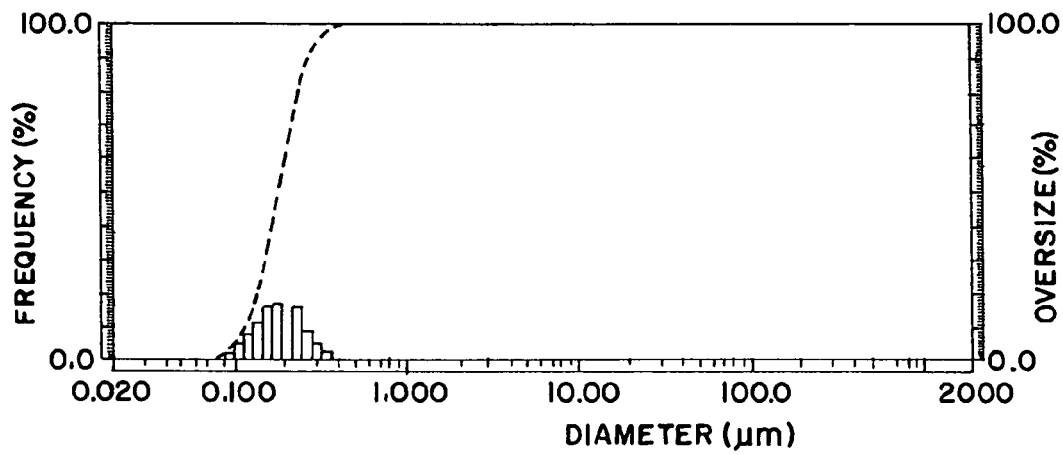
FIG. 7 shows a particle size distribution curve (Example 1)

A 1% itraconazole nanosuspension containing 0.1% poloxamer 188, 0.1% deoxycholate, and 2.2% glycerin was manufactured using a combination microprecipitation-homogenization procedure (U.S. patent application 2002/0127278 A1). The initial particle size distribution as measured by static light scattering (Horiba LA-920) is shown in FIG. 7.

Figure 8:
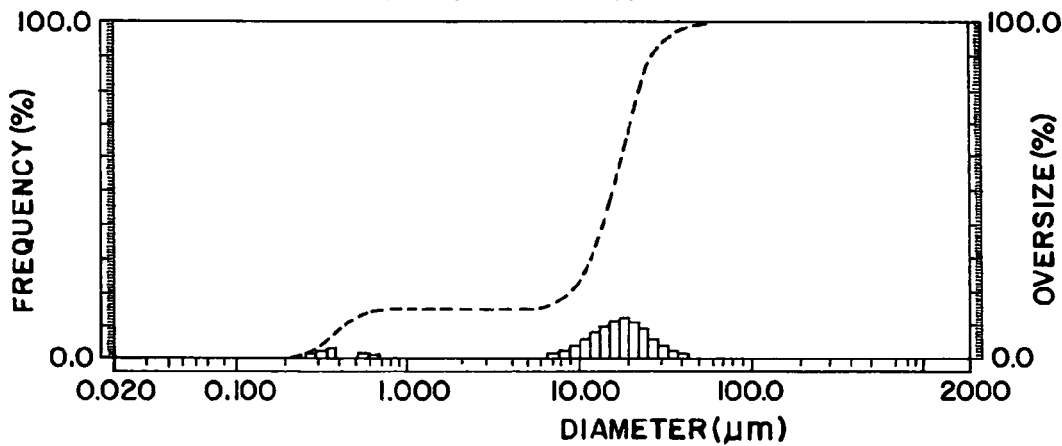
FIG. 8 shows a particle size distribution for a control sample (Example 1)

As a positive control, a 5 ml sample of the nanosuspension was first sterilized using a normal autoclaving cycle of 121° C. for 15 minutes. This resulted in significant aggregation of the particles, as shown by the light scattering data in FIG. 8. Aggregation of this sort is typical for nanosuspensions stabilized with surfactants whose cloud point is less than 121° C. (Cloud point of Poloxamer 188=~110° C.).

In contrast, when the same nanosuspension was sterilized using the high-pressure sterilization cycle shown in FIG. 9, the resulting particle size distribution of the 1% itraconazole nanosuspension remained completely unchanged, as shown in FIG. 10.

VII. High Pressure Sterilization Equipment and Methodologies

High-pressure sterilization instruments typically have a sterilization chamber with temperature and pressure controls. The chamber has a lid which is closed tight while in use. The apparatus is capable of reaching pressures up to 1000 Mpa. The apparatus also has a heat source that can heat the sterilization chamber to 120° C. and above.

The method for using the apparatus includes the steps of providing a system in a desired form. In the case of pharmaceutical preparations, the preparation will be a powder form, solution or as an aqueous particle dispersion. In a preferred form of the invention, the pharmaceutical preparation is contained within a container which changes in volume or shape in response to pressure applied to the container. Such containers can include a flexible polymeric container or other flexible container such as a syringe barrel, cartridge for a jet injector or a metered dose inhaler. These containers will be discussed in greater detail below. The present invention further contemplates adding the pharmaceutical preparation directly to the sterilization chamber.

The pharmaceutical preparation is inserted into the sterilization chamber where the preparation will be subjected to a change in pressure, a change in temperature or both simultaneously. Unlike present autoclaves for sterilizing I.V. containers and the like which only reach pressures less than 0.25 Mpa, the present method subjects the preparation to pressures in excess of 0.25 Mpa. In a preferred form of the invention the preparations will be subjected to pressures from above 0.25 Mpa to about 1500 Mpa, more preferable from 0.25 Mpa to about 700 Mpa and any range or combination of ranges therein.

The present invention further includes applying temperature and pressure so as to minimize the period the preparation is exposed to temperatures in excess of 25° C. Preferably, the temperature of the system will be in excess of 70° C., more preferably 90° C., more preferably 100° C. and most preferably 120° C. and higher. Various temperature-time-pressure profiles such as the one shown in FIG. 6 can be employed to sterilize the preparation without causing a change from the stable state to the unstable state of the preparation.

Figure 6:
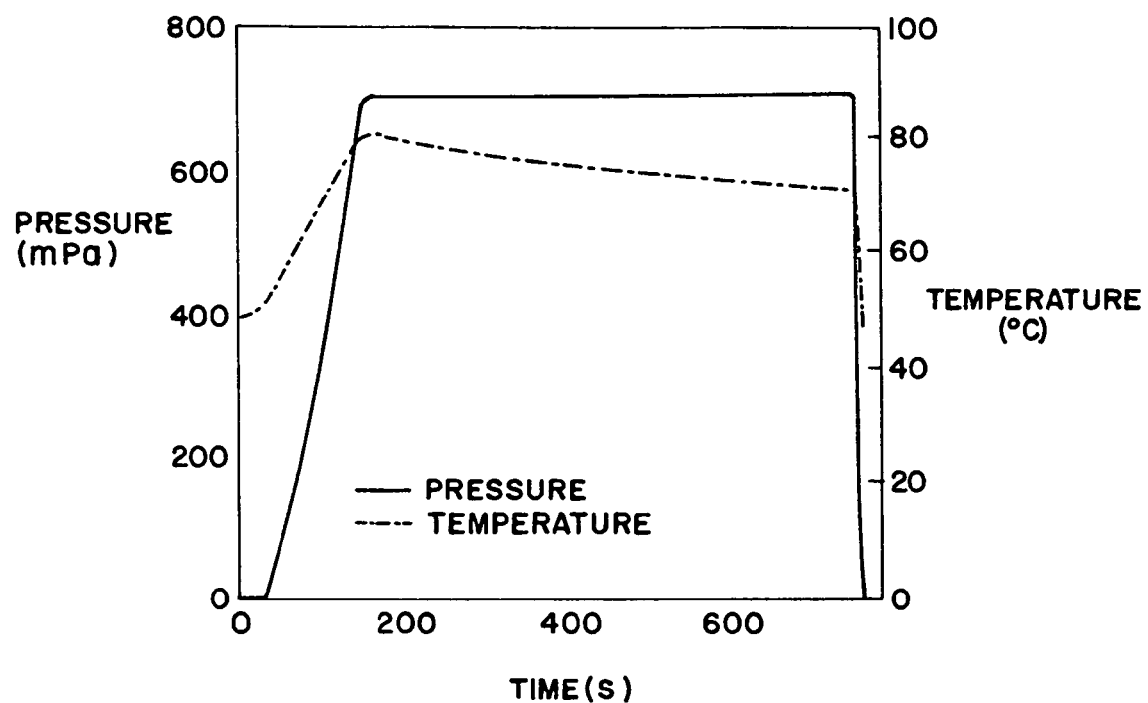
FIG. 6 shows a pressure-time-temperature profile.

In particular, FIG. 6 shows a temperature-time-pressure profile where a pharmaceutical preparation is exposed to pressures of about 700 Mpa and energy is added to raise the temperature to about 121° C. for a period in a first cycle, followed by a second cycle of lowering the pressure to atmospheric pressure and lowering the pressure to room temperature for a period. FIG. 6 shows the preparation experiences rapid temperature changes during each pressure pulse. These temperature changes are induced by instantaneous adiabatic heating and cooling of the product from compression and decompression, respectively. Typical times to achieve sterility are on the order of minutes, where 2 or more cycles are used.

The pharmaceutical preparation is considered sterilized when the probability of a non-sterile unit is equal to or less than one in a million. This satisfies United States, European and Japanese pharmacopoeia requirements.

VIII. Lethality of the Sterilization Process

The 1% itraconazole nanosuspension processed above using a high-pressure sterilization cycle is currently being tested for sterility. In saline, the effect of high-pressure sterilization on the lethality of *Bacillus stearothermophilus* has already been demonstrated (using the most heat-resistant of the strains mentioned to have demonstrated high moist heat resistance with respect to bioburden—see reference ANSI/AAMI/ISO 11134-1993, Sterilization of health care products—Requirements for validation and routine control—Industrial moist heat sterilization. American National Standard developed by the Association for the advancement of medical instrumentation and approved by the American National Standards Institute, page 12, section A.6.6.). Test and control units inoculated with at least one million spores of *Bacillus stearothermophilus* were subjected to two different processes—the first process used a pressure of approximately 600 MPa for 1-minute and the second process used a pressure of approximately 600 MPa for six 10-second cycles. The initial and highest temperatures in both processes were 90° C. and 121° C., respectively. No survivors were found in the saline solutions for both processes (see Table 1). It is anticipated that similar results will be found when the 1% itraconazole nanosuspension is inoculated and sterilized.

TABLE 1

Lethality of *Bacillus stearothermophilus* in Two High-Pressure Sterilization Processes

| Solution | Sterilization Conditions | CFU/ml |
|---|---|---|
| Saline Solution 1 - Control | None | $1.9E10^6$ |
| Saline Solution 1 - Sterilized | 600 MPa, One 1-minute cycle, Initial Temperature = 90° C., High Pressure Temperature = 121° C. | 0 |
| Saline Solution 2 - Control | None | $3.7E10^6$ |
| Saline Solution 2 - Sterilized | 600 MPa, Six 10-second cycles, Initial Temperature = 90° C., High Pressure Temperature = 121° C. | 0 |

IX. Containers

Various containers, preferably those used as medical devices (e.g., for pharmaceutical administration, renal dialysis and blood collecting/processing can be sterilized by methods of the present invention. Examples of such containers include, but are not limited to, fluid administration sets (including those containing syringes), blood collection assemblies (e.g., blood pack units), disposable assemblies for automated blood processing, dialyzer assemblies, and peritoneal dialysis bags, catheters and assemblies. Typically such systems will contain a fluid transfer member (e.g., tubing).

FIG. 11 shows a flowable materials container 150 having two side walls 152 defining a chamber 154 therebetween. An access member 155 provides for sterile access to the contents of the container. FIG. 12 shows a multiple chamber container 160 having a first and second chambers 162, 164 connected by a peel seal 166. Such multichamber containers are particularly suitable for storing a liquid in one chamber and a powder in the second chamber or liquid in both chambers. The peel seal allows for mixing of the components just prior to usage. Suitable multiple chamber containers include, but are not limited to, those disclosed in U.S. Pat. Nos. 5,577,369, 6,017,598, incorporated herein by reference and made a part hereof. The method of claim 1 wherein the container is selected from the group consisting of a sealed fluid container, a syringe and a sealed tubing.

Figure 13:
FIG. 13 shows a monolayer film.
Figure 14:
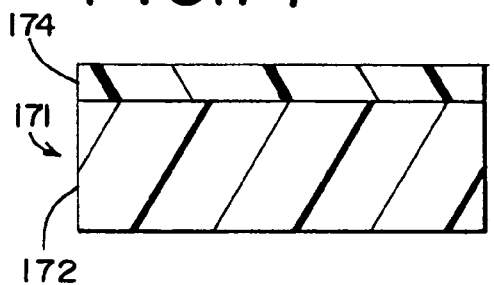
FIG. 14 shows a two-layer film.

In a preferred form of the invention, the side walls are made from a non-PVC containing polymer. The side walls can be formed from a monolayer structure 170 (FIG. 13) or a multiple layer 171 having a first and second layer 174, 176 as shown in FIG. 14. It is contemplated having more than 2 layers in the film. In another form of the invention, the side walls are non-oriented and are not considered heat-shrinkable films.

Suitable non-PVC containing polymers for forming the side walls include polyolefins, ethylene and lower alkyl acrylate copolymers, ethylene and lower alkyl substituted alkyl acrylate copolymers, ethylene vinyl acetate copolymers, polybutadienes, polyesters, polyamides, and styrene and hydrocarbon copolymers.

Suitable polyolefins include homopolymers and copolymers obtained by polymerizing alpha-olefins containing from 2 to 20 carbon atoms, and more preferably from 2 to 10 carbons. Therefore, suitable polyolefins include polymers and copolymers of propylene, ethylene, butene-1, pentene-1, 4-methyl-1-pentene, hexene-1, heptene-1, octene-1, nonene-1 and decene-1. Most preferably the polyolefin is a homopolymer or copolymer of propylene or a homopolymer or copolymer of polyethylene.

Suitable homopolymers of polypropylene can have a stereochemistry of amorphous, isotactic, syndiotactic, atactic, hemiisotactic or stereoblock. In one preferred form of the invention the homopolymer of polypropylene is obtained using a single site catalyst.

Suitable copolymers of propylene are obtained by polymerizing a propylene monomer with an α-olefin having from 2 to 20 carbons. In a more preferred form of the invention, the propylene is copolymerized with ethylene in an amount by weight from about 1% to about 20%, more preferably from about 1% to about 10% and most preferably from 2% to about 5% by weight of the copolymer. The propylene and ethylene copolymers may be random or block copolymers. In a preferred form of the invention, the propylene copolymer is obtained using a single-site catalyst.

It is also possible to use a blend of polypropylene and α-olefin copolymers wherein the propylene copolymers can vary by the number of carbons in the α-olefin. For example, the present invention contemplates blends of propylene and α-olefin copolymers wherein one copolymer has a 2 carbon α-olefin and another copolymer has a 4 carbon α-olefin. It is also possible to use any combination of α-olefins from 2 to 20 carbons and more preferably from 2 to 8 carbons. Accordingly, the present invention contemplates blends of propylene and α-olefin copolymers wherein a first and second α-olefins have the following combination of carbon numbers: 2 and 6, 2 and 8, 4 and 6, 4 and 8. It is also contemplated using more than 2 polypropylene and α-olefin copolymers in the blend. Suitable polymers can be obtained using a catalloy procedure.

It may also be desirable to use a high melt strength polypropylene. High melt strength polypropylenes can be a homopolymer or copolymer of polypropylene having a melt flow index within the range of 10 grams/10 min. to 800 grams/10 min., more preferably 30 grams/10 min. to 200 grams/10 min, or any range or combination of ranges therein. High melt strength polypropylenes are known to have free-end long chain branches of propylene units. Methods of preparing polypropylenes which exhibit a high melt strength characteristic have been described in U.S. Pat. Nos. 4,916,198; 5,047,485; and 5,605,936 which are incorporated herein by reference and made a part hereof. One such method includes irradiating a linear propylene polymer in an environment in which the active oxygen concentration is about 15% by volume with high energy ionization energy radiation at a dose of 1 to $10^4$ megarads per minute for a period of time sufficient for a substantial amount of chain scission of the linear propylene polymer to occur but insufficient to cause the material to become gelatinous. The irradiation results in chain scission. The subsequent recombination of chain fragments results in the formation of new chains, as well as joining chain fragments to chains to form branches. This further results in the desired free-end long chain branched, high molecular weight, non-linear, propylene polymer material. Radiation is maintained until a significant amount of long chain branches form. The material is then treated to deactivate substantially all the free radicals present in the irradiated material.

High melt strength polypropylenes can also be obtained as described in U.S. Pat. No. 5,416,169, which is incorporated in its entirety herein by reference and made a part hereof, when a specified organic peroxide (di-2-ethylhexyl peroxydicarbonate) is reacted with a polypropylene under specified conditions, followed by melt-kneading. Such polypropylenes are linear, crystalline polypropylenes having a branching coefficient of substantially 1, and, therefore, has no free end long-chain branching and will have a intrinsic viscosity of from about 2.5 dl/g to 10 dl/g.

Suitable homopolymers of ethylene include those having a density of greater than 0.915 g/cc and includes low density polyethylene (LDPE), medium density polyethylene (MDPE) and high density polyethylene (HDPE).

Suitable copolymers of ethylene are obtained by polymerizing ethylene monomers with an α-olefin having from 3 to 20 carbons, more preferably 3-10 carbons and most preferably from 4 to 8 carbons. It is also desirable for the copolymers of ethylene to have a density as measured by ASTM D-792 of less than about 0.915 g/cc and more preferably less than about 0.910 g/cc and even more preferably less than about 0.900 g/cc. Such polymers are oftentimes referred to as VLDPE (very low density polyethylene) or ULDPE (ultra low density polyethylene). Preferably the ethylene α-olefin copolymers are produced using a single site catalyst and even more preferably a metallocene catalyst systems. Single site catalysts are believed to have a single, sterically and electronically equivalent catalyst position as opposed to the Ziegler-Natta type catalysts which are known to have a mixture of catalysts sites. Such single-site catalyzed ethylene α-olefins are sold by Dow under the trade name AFFINITY, DuPont Dow under the trademark ENGAGE® and by Exxon under the trade name EXACT. These copolymers shall sometimes be referred to herein as m-ULDPE.

Suitable copolymers of ethylene also include ethylene and lower alkyl acrylate copolymers, ethylene and lower alkyl substituted alkyl acrylate copolymers and ethylene vinyl acetate copolymers having a vinyl acetate content of from about 8% to about 40% by weight of the copolymer. The term "lower alkyl acrylates" refers to comonomers having the formula set forth in Diagram 1:

Diagram 1

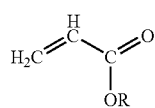

The R group refers to alkyls having from 1 to 17 carbons. Thus, the term "lower alkyl acrylates" includes but is not limited to methyl acrylate, ethyl acrylate, butyl acrylate and the like.

The term "alkyl substituted alkyl acrylates" refers to comonomers having the formula set forth in Diagram 2:

Diagram 2

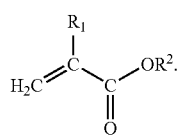

$R_1$ and $R_2$ are alkyls having 1-17 carbons and can have the same number of carbons or have a different number of carbons. Thus, the term "alkyl substituted alkyl acrylates" includes but is not limited to methyl methacrylate, ethyl methacrylate, methyl ethacrylate, ethyl ethacrylate, butyl methacrylate, butyl ethacrylate and the like.

Suitable polybutadienes include the 1,2- and 1,4-addition products of 1,3-butadiene (these shall collectively be referred to as polybutadienes). In a more preferred form of the invention, the polymer is a 1,2-addition product of 1,3 butadiene (these shall be referred to as "1,2 polybutadienes"). In an even more preferred form of the invention, the polymer of interest is a syndiotactic 1,2-polybutadiene and even more preferably a low crystallinity, syndiotactic 1,2 polybutadiene. In a preferred form of the invention, the low crystallinity, syndiotactic 1,2 polybutadiene will have a crystallinity less than 50%, more preferably less than about 45%, even more preferably less than about 40%, even more preferably the crystallinity will be from about 13% to about 40%, and most preferably from about 15% to about 30%. In a preferred form of the invention, the low crystallinity, syndiotactic 1,2 polybutadiene will have a melting point temperature measured in accordance with ASTM D 3418 from about 70° C. to about 120° C. Suitable resins include those sold by JSR (Japan Synthetic Rubber) under the grade designations: JSR RB 810, JSR RB 820, and JSR RB 830.

Suitable polyesters include polycondensation products of di- or polycarboxylic acids and di or poly hydroxy alcohols or alkylene oxides. In a preferred form of the invention, the polyester is a polyester ether. Suitable polyester ethers are obtained from reacting 1,4 cyclohexane dimethanol, 1,4 cyclohexane dicarboxylic acid and polytetramethylene glycol ether and shall be referred to generally as PCCE. Suitable PCCE's are sold by Eastman under the trade name ECDEL.

Suitable polyesters further include polyester elastomers which are block copolymers of a hard crystalline segment of polybutylene terephthalate and a second segment of a soft (amorphous) polyether glycols. Such polyester elastomers are sold by Du Pont Chemical Company under the trade name HYTREL®.

Suitable polyamides include those that result from a ring-opening reaction of lactams having from 4-12 carbons. This group of polyamides therefore includes nylon 6, nylon 10 and nylon 12. Acceptable polyamides also include aliphatic polyamides resulting from the condensation reaction of di-amines having a carbon number within a range of 2-13, aliphatic polyamides resulting from a condensation reaction of di-acids having a carbon number within a range of 2-13, polyamides resulting from the condensation reaction of dimer fatty acids, and amide containing copolymers. Thus, suitable aliphatic polyamides include, for example, nylon 6,6 nylon 6,10 and dimer fatty acid polyamides.

The styrene of the styrene and hydrocarbon copolymer includes styrene and the various substituted styrenes including alkyl substituted styrene and halogen substituted styrene. The alkyl group can contain from 1 to about 6 carbon atoms. Specific examples of substituted styrenes include alpha-methylstyrene, beta-methylstyrene, vinyltoluene, 3-methylstyrene, 4-methylstyrene, 4-isopropylstyrene, 2,4-dimethylstyrene, o-chlorostyrene, p-chlorostyrene, o-bromostyrene, 2-chloro-4-methylstyrene, etc. Styrene is the most preferred.

The hydrocarbon portion of the styrene and hydrocarbon copolymer includes conjugated dienes. Conjugated dienes which may be utilized are those containing from 4 to about 10 carbon atoms and more generally, from 4 to 6 carbon atoms. Examples include 1,3-butadiene, 2-methyl-1,3-butadiene (isoprene), 2,3-dimethyl-1,3-butadiene, chloroprene, 1,3-pentadiene, 1,3-hexadiene, etc. Mixtures of these conjugated dienes also may be used such as mixtures of butadiene and isoprene. The preferred conjugated dienes are isoprene and 1,3-butadiene.

The styrene and hydrocarbon copolymers can be block copolymers including di-block, tri-block, multi-block, star block, and mixtures thereof. Specific examples of diblock copolymers include styrene-butadiene, styrene-isoprene, and the hydrogenated derivatives thereof. Examples of triblock polymers include styrene-butadiene-styrene, styrene-isoprene-styrene, alpha-methylstyrene-butadiene-alpha-methylstyrene, and alpha-methylstyrene-isoprene-alpha-methylstyrene and hydrogenated derivatives thereof.

The selective hydrogenation of the above block copolymers may be carried out by a variety of well known processes including hydrogenation in the presence of such catalysts as Raney nickel, noble metals such as platinum, palladium, etc., and soluble transition metal catalysts. Suitable hydrogenation processes which can be used are those wherein the diene-containing polymer or copolymer is dissolved in an inert hydrocarbon diluent such as cyclohexane and hydrogenated by reaction with hydrogen in the presence of a soluble hydrogenation catalyst. Such procedures are described in U.S. Pat. Nos. 3,113,986 and 4,226,952, the disclosures of which are incorporated herein by reference and made a part hereof.

Particularly useful hydrogenated block copolymers are the hydrogenated block copolymers of styrene-isoprene-styrene, such as a styrene-(ethylene/propylene)-styrene block polymer. When a polystyrene-polybutadiene-polystyrene block copolymer is hydrogenated, the resulting product resembles a regular copolymer block of ethylene and 1-butene (EB). As noted above, when the conjugated diene employed is isoprene, the resulting hydrogenated product resembles a regular copolymer block of ethylene and propylene (EP). One example of a commercially available selectively hydrogenated is KRATON G-1652 which is a hydrogenated SBS triblock comprising 30% styrene end blocks and a midblock equivalent is a copolymer of ethylene and 1-butene (EB). This hydrogenated block copolymer is often referred to as SEBS. Kraton G-1657 is a blend of SEBS triblock and SBS diblock which is also suitable. Other suitable SEBS or SIS copolymers are sold by Kurary under the tradename SEPTON® and HYBRAR®.

It may also be desirable to use graft modified styrene and hydrocarbon block copolymers by grafting an alpha,beta-unsaturated monocarboxylic or dicarboxylic acid reagent onto the selectively hydrogenated block copolymers described above.

The block copolymers of the conjugated diene and the vinyl aromatic compound are grafted with an alpha,beta-unsaturated monocarboxylic or dicarboxylic acid reagent. The carboxylic acid reagents include carboxylic acids per se and their functional derivatives such as anhydrides, imides, metal salts, esters, etc., which are capable of being grafted onto the selectively hydrogenated block copolymer. The grafted polymer will usually contain from about 0.1 to about 20%, and preferably from about 0.1 to about 10% by weight based on the total weight of the block copolymer and the carboxylic acid reagent of the grafted carboxylic acid. Specific examples of useful monobasic carboxylic acids include acrylic acid, methacrylic acid, cinnamic acid, crotonic acid, acrylic anhydride, sodium acrylate, calcium acrylate and magnesium acrylate, etc. Examples of dicarboxylic acids and useful derivatives thereof include maleic acid, maleic anhydride, fumaric acid, mesaconic acid, itaconic acid, citraconic acid, itaconic anhydride, citraconic anhydride, monomethyl maleate, monosodium maleate, etc.

The styrene and hydrocarbon block copolymer can be modified with an oil such as the oil modified SEBS sold by the Shell Chemical Company under the product designation KRATON G2705.

It is also contemplated the films can be formed from polymer blends of the components described above. Particularly suitable polymeric blends are disclosed in U.S. Pat. No. 5,849,843, which is incorporated herein by reference and made a part hereof. In a preferred form of the invention one layer will be fabricated from a blend having 2 components or more and more preferably three or more components. These polymer blends can form a single layer film or can be incorporated into multiple layer films as described in U.S. Pat. No. 5,998,019, which is incorporated herein by reference and made a part hereof.

Three Component Compositions

In a first embodiment of a three component system, the first component will confer heat resistance and flexibility to the composition. This component may be chosen from the group consisting of amorphous polyalpha-olefins and preferably is a flexible polyolefin. These polyolefins should resist distortions to high temperatures up to 121° C., having a peak melting point of greater than 130° C. and be highly flexible, having a modulus of not more than 40,000 psi and more preferably, not more than 20,000 psi. In addition, certain polypropylenes with high syndiotacticity also posses the properties of high melting point and low modulus. The first component should constitute by weight within the range of 40-90% by weight of the composition.

The second component of the three component composition is an RF susceptible polymer which confers RF sealability to the composition and may be selected from either of two groups of polar polymers. The first group consists of ethylene copolymers having 50-85% ethylene content with comonomers selected from the group consisting of acrylic acid, methacrylic acid, ester derivatives of acrylic acid with alcohols having 1-10 carbons, ester derivatives of methacrylic acid with alcohols having 1-10 carbons, vinyl acetate, and vinyl alcohol. The RF susceptible polymer may also be selected from a second group consisting of polymers containing segments of polyurethane, polyester, polyurea, polyimide, polysulfones, and polyamides. These functionalities may constitute between 5-100% of the RF susceptible polymer. The RF susceptible polymer should constitute by weight within the range of 5-50% of the composition.

Preferably, the RF component is copolymers of ethylene methyl acrylate with methyl acrylate within the range of 15-25% by weight of the polymer. The final component of the three component compound ensures compatibility between the first two components, and is selected from an styrenic block copolymers and preferably is maleic anhydride functionalized. The third component should constitute by weight within the range of 5-30% of the composition.

In a second embodiment of the three component film, the first component confers RF sealability and flexibility over the desired temperature range. The first component confers high temperature resistance ("temperature resistant polymer") and is chosen from the group consisting of polyamides, polyimides, polyurethanes, polypropylene and polymethylpentene. Preferably the first component constitutes by weight within the range of 30-60% of the composition, and preferably is polypropylene. The second component confers RF sealability and flexibility over the desired temperature range. The RF polymer is selected from the first and second groups identified above with the exception of ethylene vinyl alcohol. The second component should constitute by weight within the range of 30-60% of the composition. The third component ensures compatibility between the first two components and is chosen from SEBS block copolymers and preferably is maleic anhydride functionalized. The third component should constitute within the range of 5-30% by weight of the composition.

Four Component Compositions

The first component of the four component film is to confer heat resistance. This component may be chosen from polyolefins, most preferably polypropylenes, and more specifically the propylene alpha-olefin random copolymers (PPE). Preferably, the PPE's will have a narrow molecular weight range. The PPE's possess the required rigidity and the resistance to yielding at the autoclave temperatures of about 121° C. However, by themselves, the PPE's are too rigid to meet the flexibility requirements. When combined by alloying with certain low modulus polymers, good flexibility can be achieved. Examples of acceptable PPE's include those sold under the product designations Soltex 4208, and Exxon Escorene PD9272. These low modulus copolymers can include ethylene based copolymers such as ethylene-co-vinyl acetate ("EVA"), ethylene co-alpha olefins, or the so-called ultra low density (typically less than 0.90 Kg/L) polyethylenes ("ULDPE"). These ULDPE include those commercially available products sold under the trademarks TAFMER® (Mitsui Petrochemical Co.) under the product designation A485, Exact® (Exxon Chemical Company) under the product designations 4023-4024, and Insite® technology polymers (Dow Chemical Co.). In addition, polybutene-1 ("PB"), such as those sold by Shell Chemical Company under product designations PB-8010, PB-8310; thermoplastic elastomers based on SEBS block copolymers, (Shell Chemical Company), poly isobutylene ("PIB") under the product designations Vistanex L-80, L-100, L-120, L-140 (Exxon Chemical Company), ethylene alkyl acrylate, the methyl acrylate copolymers ("EMA") such as those under the product designation EMAC 2707, and DS-1130 (Chevron), and n-butyl acrylates ("ENBA") (Quantum Chemical) were found to be acceptable copolymers. Ethylene copolymers such as the acrylic and methacrylic acid copolymers and their partially neutralized salts and ionomers, such as PRIMACOR® (Dow Chemical Company) and SURYLN® (E.I. DuPont de Nemours & Company) were also satisfactory.

Typically, ethylene based copolymers have melting points of less than about 110° C. are not suited for autoclaving applications. Furthermore, only a limited range of proportions of each component allows the simultaneous fulfillment of the flexibility and autoclavability requirements. Preferably, the first component is chosen from the group of polypropylene homo and random copolymers with alpha olefins which constitute by weight approximately 30-60%, more preferably 35-45%, and most preferably 45%, of the composition. For example, random copolymers of propylene with ethylene where the ethylene content is in an amount within the range of 1-6%, and more preferably 2-4%, of the weight of the polymer is preferred as the first component.

The second component of the four component composition confers flexibility and low temperature ductility and is a second polyolefin different than that of the first component wherein it contains no propylene repeating units ("non propylene based polyolefin"). Preferably it is ethylene copolymers including ULDPE, polybutene, butene ethylene copolymers, ethylene vinyl acetate, copolymers with vinyl acetate contents between approximately 18-50%, ethylene methyl acrylate copolymers with methyl acrylate contents being between approximately 20-40%, ethylene n-butyl acrylate copolymers with n-butyl acrylate content of between 20-40%, ethylene acrylic acid copolymers with the acrylic acid content of greater than approximately 15%. An example of these products are sold under such product designations as Tafmer A-4085 (Mitsui), EMAC DS-1130 (Chevron), Exact 4023, 4024 and 4028 (Exxon), and should constitute by weight approximately 25-50%, more preferably 35-45%, and most preferably 45%, of the composition. To impart RF dielectric loss to the four component composition, certain known high dielectric loss ingredients ("RF susceptible polymers") are included in the composition. These polymers may be selected from the group of RF polymers in the first and second group set forth above.

Other RF active materials include PVC, vinylidine chlorides, and fluorides, copolymer of bis-phenol-A and epichlorohydrines known as PHENOXYS® (Union Carbide). However, significant contents of these chlorine and fluorine containing polymers would render the composition undesirable as incineration of such a material would generate inorganic acids.

The polyamides of the RF susceptible polymer are preferably selected from aliphatic polyamides resulting from the condensation reaction of di-amines having a carbon number within a range of 2-13, aliphatic polyamides resulting from a condensation reaction of di-acids having a carbon number within a range of 2-13, polyamides resulting from the condensation reaction of dimer fatty acids, and amides containing copolymers (random, block, and graft). Polyamides such as nylons are widely used in thin film material because they offer abrasion resistance to the film. However, rarely are the nylons found in the layer which contacts medical solutions as they typically contaminate the solution by leaching out into the solution. The most preferred RF susceptible polymer are a variety of dimer fatty acid polyamides sold by Henkel Corporation under the product designations MACROMELT and VERSAMID, which do not lead to such contamination. The RF susceptible polymer preferably should constitute by weight approximately 5-30%, more preferably between 7-13%, and most preferably 10%, of the composition.

The fourth component of the composition confers compatibility between the polar and non-polar components of the composition (sometimes referred to as a "compatibilizing polymer") and preferably is styrenic block copolymers with hydrocarbon soft segments. More preferably, the fourth component was chosen from SEBS block copolymers that are modified by maleic anhydride, epoxy, or carboxylate functionalities, and preferably is an SEBS block copolymer that contains maleic anhydride functional groups ("functionalized"). Such a product is sold by Shell Chemical Company under the designation KRATON RP-6509. The compatibilizing polymer should constitute by weight approximately 5-40%, more preferably 7-13%, and most preferably 10% of the composition. It may also desirable to add a fifth component of a nonfunctionalized SEBS block copolymer such as the ones sold by Shell Chemical Company under the product designations KRATON G-1652 and G-1657. The fifth component should constitute by weight approximately 5-40%, more preferably 7-13%, and most of the composition.

For each of the compositions set forth above, it may be desirable to add, in trace amounts, other additives such as slip agents, lubricants, waxes, and antiblocks as is needed and as is well known in the art as long as the final composition meets the physical requirements set forth above.

The film may be made using techniques well known in the industry. For example, the above components may be blended in the dry form in a high intensity blender such as a Welex blender and fed into an extruder. The components may also be gravimetrically fed into a high intensity mixing extruder of the twin screw design, such as a Werner Pfleiderer, and the output may be quenched in multiple strands in a water bath, pelletized, and dried for use. The pelletizing step may be avoided in a third method by feeding the output of the compounding extruder directly into a film extruder. It is also possible to build into a film extruder a high intensity mixing section so that an alloy film may be produced using a single extruder.

The multiple layer film 171 can utilize the above-described blends as one layer 172 and another layer as 174. In one preferred form of the invention the layer 174 is a skin layer. The skin layer 174 confers heat distortion resistance and abrasion resistance and is preferably a polypropylene and more preferably a polypropylene copolymer blended with styrene and hydrocarbon block copolymers. More preferably, the skin layer 174 is a polypropylene copolymer blended with SEBS block copolymer within a range of 0-20% by weight. The skin layer 174 should have a thickness within the range of 0.2-3.0 mils thick.

Figure 15:
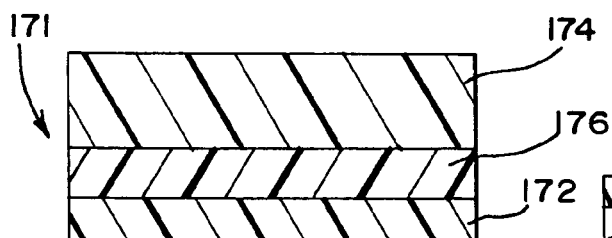
FIG. 15 shows a three layer film.

FIG. 15 shows another embodiment of the present invention having a core layer 176 interposed between the skin layer 172 and the RF layer 174. The core layer 176 confers heat distortion resistance, and flexibility to the film structure 10 and compatibility among the components of the film structure 170. Preferably, the core layer will have a thickness within the range of 0.5-10 mils and more preferably 1-4 mils. The core layer 176 includes three components. The first component is a polyolefin and preferably a polypropylene in an amount that constitutes in a range of 20-60% by weight of the core layer 176, more preferably 35-50%, and most preferably 45% of the core layer 176.

The second component of the core layer 176 is chosen from a group consisting of compounds that confer flexibility to the core layer 16 including ULDPE, polybutene copolymers. Preferably, the second component of the core layer is ULDPE or polybutene-1 in an amount by weight of 40%-60%, more preferably 40-50%, and most preferably 40%.

The third component of the core layer 176 is chosen from a group of compounds that confer compatibility among the components of the core layer 176 and includes styrene-hydrocarbon block copolymers and most preferably SEBS block copolymers. The third component is in an amount preferably within a range of 5-40% by weight of the core layer 176, more preferably 7-15%, and most preferably 15%.

It is also possible to add as a fourth component of the core layer 176, reground trim scrap material recovered during the manufacturing of containers. The scrap material is dispersed throughout the core layer 16. Scrap may be added in an amount preferably between approximately 0-50% by weight of the core layer 16, and more preferably within the range of 10-30% and most preferably within the range of 3-12%.

Figure 16:
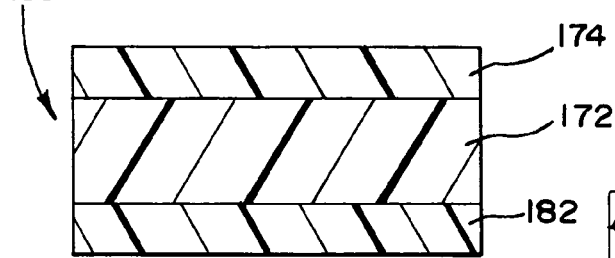
FIG. 16 shows a three layer film.

FIG. 16 shows a film 180 having a solution contact layer 182 adhered to a side of the RF layer 174 opposite the skin layer 174. The solution contact layer 182 may be of one of the materials set forth above, more preferably will contain a polyolefin, and even more preferably will be the same material as the skin layer 174 or the same material as the core layer 176. Preferably, the solution contact layer 182 has a thickness within the range of 0.2-1.0 mils and most preferably 1.0 mils.

Figure 17:
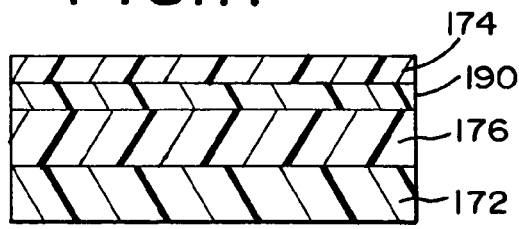
FIG. 17 shows a four layer film.
Figure 18:
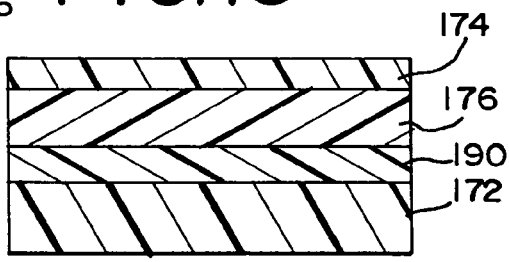
FIG. 18 shows a four layer film.
Figure 19:
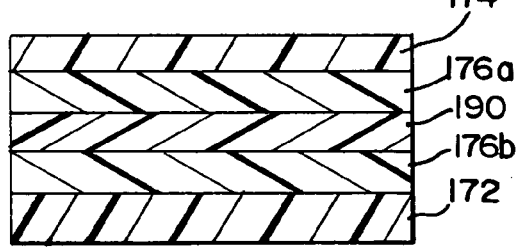
FIG. 19 shows a five layer film.

FIG. 17 shows another embodiment of the multiple layer film structure having the skin layer 174, core layer 176, and RF layer 172 as described above with an additional discrete layer of scrap 190 between the skin layer 174 and the core layer 176. FIG. 18 shows the discrete scrap layer 190 between the core layer 176 and the RF layer 172. FIG. 19 shows the scrap layer 190 dividing the core layer 176 into first and second core layers 176a and 176b. Preferably, the scrap layer 190 should have a thickness within the range of 0.5-5.0 mils and most preferably 1.0 mils.

Figure 20:
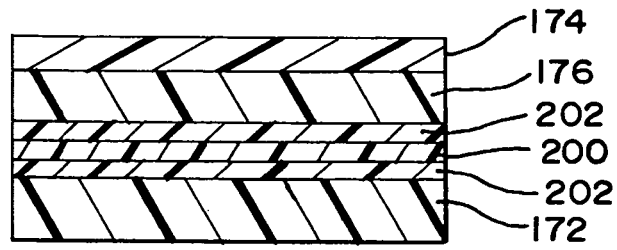
FIG. 20 shows a six layer film.
Figure 21:
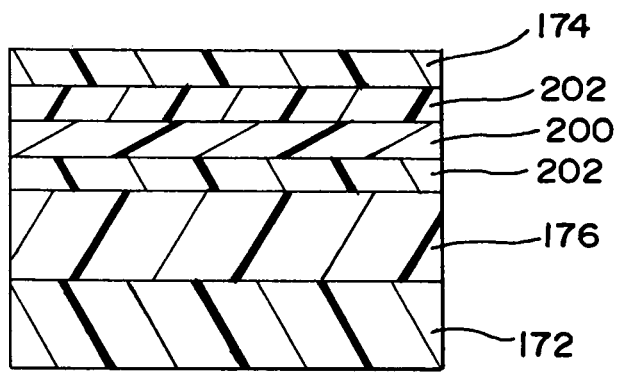
FIG. 21 shows a six layer film.
Figure 22:
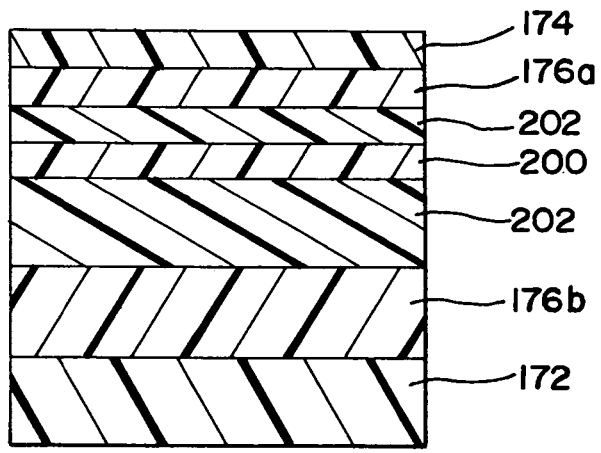
FIG. 22 shows a seven layer film.

FIG. 20 shows another embodiment of the present invention having six layers including the skin 174, core 176, and RF layers 172 discussed above, with a barrier layer 200 interposed between the core 176 and RF layers 172 and adhered thereto with tie layers 202 attached to opposite sides of the barrier layer 200. FIG. 21 shows the barrier layer 200 between the core layer 176 and the skin layer 174. FIG. 22 shows the barrier layer 200 dividing the core layer 176 into two core layers 176a and 176b. The barrier layer 200 increases the gas barrier properties of the film structure. The barrier layer 200 is selected from the group consisting ethylene vinyl alcohols such as that sold under the name Evalca (Evalca Co.), highly glassy or crystalline polyamide such as Sclar PA® (Dupont Chemical Co.), high nitrile content acrylonitrile copolymers such as Barex® sold by British Petroleum. Preferably, the barrier layer 200 is ethylene vinyl alcohol, and has a thickness within the range of 0.3-1.5 mils and most preferably 1.0 mils.

The tie layers 202 may be selected from modified ethylene and propylene copolymers such as those sold under the product designations Prexar (Quantum Chemical Co.) and Bynel (Dupont) and should have a thickness within the range of 0.2-1.0 mils and most preferably 0.5 mil.

The high-pressure sterilization techniques of the present invention are also suitable for sterilizing empty drain bags for renal CAPD applications such as the container disclosed in U.S. Pat. No. 6,004,636 which is incorporated herein by reference and made a part hereof. Other containers suitable for terminal sterilization using the high-pressure sterilization techniques of this invention include flexible cell culture containers such as those disclosed in U.S. Pat. Nos. 5,935,847, 4,417,753, 4,210,686 which are incorporated in their entirety herein by reference and made a part hereof. Protein compatible films and containers such as those disclosed in U.S. Pat. No. 6,309,723 which is incorporated herein by reference and made a part hereof, can also be sterilized using the high-pressure sterilization techniques disclosed herein. Further, the sterilization techniques are also suitable for sterilizing containers for containing oxygen sensitive compounds such as deoxygenated hemoglobin as is disclosed in U.S. Pat. No. 6,271,351, which is incorporated herein by reference and made a part hereof. Because the sterilization techniques only require exposing such containers for a short period of time to temperatures greater than 100° C. many containers that are unsuitable for terminal sterilization using standard techniques of exposing the container to steam at 121° C. for 1 hour are capable of being terminally sterilized with the high pressure techniques of the present invention.

FIG. 23 shows a syringe 220 having a barrel 222 and a plunger 224 as is well known in the art. The syringe 220 can be fabricated from the materials described above. The syringe barrel can be filled with one of the dispersions or dry powder of the pharmaceutical compound and then autoclaved as described above. The syringe barrel and preferably both the barrel and the plunger must be capable of changing volume in response to an increase pressure and both parts 222 and 224 must have sufficient heat distortion resistance to be capable of withstanding the terminal sterilization process of this invention.

FIG. 24 shows a cartridge 230 or insert having a body 232 defining a chamber 234. The chamber 234 is sealed with an end cap 236 or a pair of end caps if necessary. The cartridge can be inserted into a delivery device such as a jet injector such as those set forth in U.S. Pat. No. 6,132,395, or in other delivery device that is capable of accessing the contents of the chamber 234 and delivering the contents for use.

FIG. 25 shows a fluid access device 250 having a medical tubing 252 and an access device 254. The access device can be an object for piercing an access member 154 or can be adapted to dock or otherwise connect to the syringe barrel 222 to convey fluid from the container used for sterilization to delivery to a patient or to another device used to deliver the composition to a patient.

There are a number of containers such as certain polymeric medical containers that cannot withstand a terminal sterilization process of exposing the container to steam at 121° C. for 1 hour.

X. Products

The present invention provided sterilized products and preferably those containing pharmaceutical preparations, including, but not limited to, containers containing sterile pharmaceutical preparations, the preparation having been sterilized by supplying heat to the product and pressurizing the product to a pressures of greater than 0.25 Mpa. The present invention also provides sterile pharmaceutical preparations that are free from chemical cloud point modifiers.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

What is claimed is:

1. A method for sterilizing a dynamic dispersion system having a stable state and an unstable state comprising the steps of:
    pressurizing the dynamic dispersion system to a pressure in excess of 0.25 MPa to increase the temperature of the dynamic dispersion system to a temperature in excess of 120° C. for a period of time sufficient to achieve a sterile system, the dynamic dispersion system having micro- or nano-dispersions of small particles or droplets, the small particles or droplets having a stable state and an unstable state; and withdrawing pressure from the dynamic dispersion system of small particles or droplets before the small particles or droplets reach the unstable state, wherein the small particles or droplets comprise (i) a therapeutically active compound and (ii) an excipient, the excipient being associated with the therapeutically active compound, wherein the excipient comprises a surfactant, wherein the temperature of the dynamic dispersion system is raised above 120° C. for a time period in excess of 1 minute.

2. The method of claim 1 wherein pressure is applied to the dynamic dispersion system in pulses of varying pressure.

3. A method for sterilizing a dynamic dispersion system having a stable state and an unstable state comprising the steps of:

pressurizing the dynamic dispersion system to a pressure in excess of 0.25 MPa to increase the temperature of the dynamic dispersion system to a temperature in excess of 120° C. for a period of time sufficient to achieve a sterile system, the dynamic dispersion system having micro- or nano-dispersions of small particles or droplets, the small particles or droplets having a stable state and an unstable state; and withdrawing pressure from the dynamic dispersion system of small particles or droplets before the small particles or droplets reach the unstable state, wherein the small particles or droplets comprise (i) a therapeutically active compound and (ii) an excipient, the excipient being associated with the therapeutically active compound, wherein the excipient comprises a surfactant, wherein the step of pressurizing the system is pulsed.

4. A method for sterilizing a dynamic dispersion system having a stable state and an unstable state comprising the steps of:

pressurizing the dynamic dispersion system to a pressure in excess of 0.25 MPa to increase the temperature of the dynamic dispersion system to a temperature in excess of 120° C. for a period of time sufficient to achieve a sterile system, the dynamic dispersion system having micro- or nano-dispersions of small particles or droplets, the small particles or droplets having a stable state and an unstable state; and withdrawing pressure from the dynamic dispersion system of small particles or droplets before the small particles or droplets reach the unstable state, wherein the small particles or droplets comprise (i) a therapeutically active compound and (ii) an excipient, the excipient being associated with the therapeutically active compound, wherein the excipient comprises a surfactant, and the small particles or droplets transform from a first thermodynamic phase into a second thermodynamic phase following the withdrawal of pressure.

5. The method of claim 1 wherein the dynamic dispersion system further comprises a vehicle.

6. The method of claim 1 wherein sterility is established when the probability of a non-sterile system is equal to or less than one in a million.

7. The method of claim 5 wherein the vehicle is an aqueous solution, an organic solvent, or an oil.

8. The method of claim 1 wherein the therapeutic compound is a solid, a liquid or a gas.

9. The method of claim 1 wherein the small particles or droplets have an average effective size of less than 100 microns.

10. The method of claim 1 wherein the small particles or droplets have an average effective size of less than 10 microns.

11. The method of claim 1 wherein the small particles or droplets have an average effective size of less than 7 microns.

12. The method of claim 1 wherein the small particles or droplets have an average effective size of less than 3 microns.

13. The method of claim 1 wherein the small particles or droplets have an average effective size of less than 1 micron.

14. The method of claim 1 wherein the small particles or droplets have an average effective size of less than 500 nm.

15. The method of claim 1 wherein the excipient is associated with the small particles or droplets in a manner selected from the group consisting of: covalently bonded thereto, ionically bonded thereto, electronically attracted thereto, adsorbed on a surface thereof, and suspended therein.

16. The method of claim 1 wherein the surfactant is selected from the group consisting of one or more of an anionic, cationic, nonionic and zwitterionic surfactants and biological surface-active molecules.

17. The method of claim 1 wherein the first and second thermodynamic phases are selected from the group consisting of crystalline, semi-crystalline, amorphous and supercooled liquid.

18. The method of claim 17 wherein the difference in the first and second thermodynamic phases is from a first crystalline structure to a second crystalline structure different from the first crystalline structure.

19. The method of claim 1 further comprising supplying heat to the dynamic dispersion system through additional heating.

20. A method for sterilizing a dynamic dispersion system having a stable state and an unstable state comprising the steps of:

pressurizing the dynamic dispersion system to a pressure in excess of 0.25 MPa to increase the temperature of the dynamic dispersion system to a temperature in excess of 120° C. for a period of time sufficient to achieve a sterile system, the dynamic dispersion system having micro- or nano-dispersions of small particles or droplets, the small particles or droplets having a stable state and an unstable state; and withdrawing pressure from the dynamic dispersion system of small particles or droplets before the small particles or droplets reach the unstable state, wherein the small particles or droplets comprise (i) a therapeutically active compound and (ii) an excipient, the excipient being associated with the therapeutically active compound, wherein the excipient comprises a surfactant, wherein the therapeutically active compound is poorly water-soluble.

21. The method of claim 20, wherein the therapeutically active compound has a solubility in water of less than about 10 mg/mL.

\* \* \* \* \*

UNITED STATES PATENT AND TRADEMARK OFFICE
CERTIFICATE OF CORRECTION

| | |
|---|---|
| PATENT NO. | : 8,617,467 B2 |
| APPLICATION NO. | : 10/946885 |
| DATED | : December 31, 2013 |
| INVENTOR(S) | : Rodriguez et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1584 days.

Signed and Sealed this
Twenty-sixth Day of May, 2015

Michelle K. Lee
*Director of the United States Patent and Trademark Office*